(12) United States Patent
Chanduszko

(10) Patent No.: US 7,431,729 B2
(45) Date of Patent: Oct. 7, 2008

(54) PATENT FORAMEN OVALE (PFO) CLOSURE DEVICE WITH RADIAL AND CIRCUMFERENTIAL SUPPORT

(75) Inventor: Andrzej J. Chanduszko, Weymouth, MA (US)

(73) Assignee: NMT Medical, Inc., Boston, MA (US)

( * ) Notice: Subject to any disclaimer, the term of this patent is extended or adjusted under 35 U.S.C. 154(b) by 81 days.

(21) Appl. No.: 10/455,572

(22) Filed: Jun. 5, 2003

(65) Prior Publication Data

US 2004/0073242 A1    Apr. 15, 2004

Related U.S. Application Data

(60) Provisional application No. 60/386,327, filed on Jun. 5, 2002.

(51) Int. Cl.
*A61B 17/08* (2006.01)
(52) U.S. Cl. .................. 606/213; 606/214; 606/215; 606/216; 606/217; 606/1
(58) Field of Classification Search ............... 600/213, 600/215, 139, 151, 232, 220, 32; 623/32; 604/285, 286
See application file for complete search history.

(56) References Cited

U.S. PATENT DOCUMENTS

| | | |
|---|---|---|
| 3,824,631 A | 7/1974 | Burstein et al. |
| 3,874,388 A | 4/1975 | King et al. ................. 128/334 |
| 3,875,648 A | 4/1975 | Bone ........................... 29/417 |
| 3,924,631 A | 12/1975 | Mancusi |

(Continued)

FOREIGN PATENT DOCUMENTS

DE    9413645 U1    10/1994

(Continued)

OTHER PUBLICATIONS

Nat'l Aeronautics and Space Administration, "55-Nitinol—The Alloy with a Memory: Its Physical Metallurgy, Properties, and Applications," A Report, pp. 24-25.

(Continued)

*Primary Examiner*—Linda Dvorak
*Assistant Examiner*—Matthew J Kasztejna
(74) *Attorney, Agent, or Firm*—Wilmer Cutler Pickering Hale & Dorr LLP

(57) ABSTRACT

The present invention provides a device for occluding an anatomical aperture, such as a septal defect or patent foramen ovale (PFO). The occluder includes two sides connected by an intermediate joint. Each of the sides includes at least one elongate element, which is arranged to form non-overlapping loops. Each loop has at least one radially-extending segment that is adjacent to a radially-extending segment of another loop. In at least some embodiments, at least one pair of adjacent radially-extending segments is connected. The loops of the device may be of various shapes, sizes, and configurations, and, in at least some embodiments, the loops have rounded peripheries. In some embodiments, at least one of the sides includes a tissue scaffold. When the occluder is deployed in vivo, the two sides are disposed on opposite sides of the septal tissue surrounding the aperture, thereby exerting a compressive force on the septal tissue that is distributed along both the outer periphery of the occluder and the radially-extending segments.

24 Claims, 13 Drawing Sheets

U.S. PATENT DOCUMENTS

| | | | | |
|---|---|---|---|---|
| 4,006,747 | A | 2/1977 | Kronenthal et al. | 128/335 |
| 4,007,743 | A | 2/1977 | Blake | 128/334 |
| 4,149,327 | A | 4/1979 | Hammer et al. | |
| 4,425,908 | A | 1/1984 | Simon | 128/1 |
| 4,610,674 | A | 9/1986 | Suzuki et al. | |
| 4,626,245 | A | 12/1986 | Weinstein | |
| 4,696,300 | A | 9/1987 | Anderson | 128/334 |
| 4,710,192 | A | 12/1987 | Liotta et al. | |
| 4,836,204 | A | 6/1989 | Landymore et al. | 128/334 |
| 4,840,623 | A | 6/1989 | Quackenbush | |
| 4,902,508 | A | 2/1990 | Badylak et al. | |
| 4,915,107 | A | 4/1990 | Rebuffat et al. | 606/144 |
| 4,917,089 | A | 4/1990 | Sideris | |
| 4,956,178 | A | 9/1990 | Badylak et al. | |
| 5,021,059 | A | 6/1991 | Kensey et al. | 606/213 |
| 5,037,433 | A | 8/1991 | Wilk et al. | 606/139 |
| 5,041,129 | A | 8/1991 | Hayhurst et al. | 606/232 |
| 5,078,736 | A | 1/1992 | Behl | |
| 5,106,913 | A | 4/1992 | Yamaguchi et al. | |
| 5,108,420 | A | 4/1992 | Marks | 606/213 |
| 5,149,327 | A | 9/1992 | Oshiyama | |
| 5,167,363 | A | 12/1992 | Adkinson et al. | |
| 5,167,637 | A | 12/1992 | Okada et al. | |
| 5,171,259 | A | 12/1992 | Inoue | |
| 5,192,301 | A | 3/1993 | Kamiya et al. | 606/213 |
| 5,222,974 | A | 6/1993 | Kensey et al. | 606/213 |
| 5,226,879 | A | 7/1993 | Ensminger et al. | |
| 5,236,440 | A | 8/1993 | Hlavacek | 606/219 |
| 5,245,023 | A | 9/1993 | Peoples et al. | |
| 5,245,080 | A | 9/1993 | Aubard et al. | |
| 5,250,430 | A | 10/1993 | Peoples et al. | |
| 5,257,637 | A | 11/1993 | El Gazayerli | 128/898 |
| 5,275,826 | A | 1/1994 | Badylak et al. | |
| 5,282,827 | A | 2/1994 | Kensey et al. | 606/215 |
| 5,284,488 | A | 2/1994 | Sideris | 606/213 |
| 5,304,184 | A | 4/1994 | Hathaway et al. | 606/144 |
| 5,312,341 | A | 5/1994 | Turi | |
| 5,312,435 | A | 5/1994 | Nash et al. | 606/213 |
| 5,316,262 | A | 5/1994 | Koebler | |
| 5,334,217 | A | 8/1994 | Das | 606/213 |
| 5,350,363 | A | 9/1994 | Goode et al. | |
| 5,350,399 | A * | 9/1994 | Erlebacher et al. | 606/213 |
| 5,354,308 | A | 10/1994 | Simon et al. | 606/198 |
| 5,411,481 | A | 5/1995 | Allen et al. | 606/144 |
| 5,413,584 | A | 5/1995 | Schulze | 606/219 |
| 5,417,699 | A | 5/1995 | Klein et al. | 606/144 |
| 5,425,744 | A | 6/1995 | Fagan et al. | 606/213 |
| 5,433,727 | A | 7/1995 | Sideris | |
| 5,451,235 | A | 9/1995 | Lock et al. | 606/213 |
| 5,478,353 | A | 12/1995 | Yoon | 606/213 |
| 5,480,353 | A | 1/1996 | Garza, Jr. | |
| 5,480,424 | A | 1/1996 | Cox | |
| 5,486,193 | A | 1/1996 | Bourne et al. | |
| 5,507,811 | A | 4/1996 | Koike et al. | 623/11 |
| 5,534,432 | A | 7/1996 | Peoples et al. | |
| 5,540,712 | A | 7/1996 | Kleshinski et al. | 606/198 |
| 5,562,632 | A | 10/1996 | Davila et al. | |
| 5,577,299 | A | 11/1996 | Thompson et al. | |
| 5,601,571 | A | 2/1997 | Moss | 606/139 |
| 5,618,311 | A | 4/1997 | Gryskiewicz | 606/216 |
| 5,620,461 | A | 4/1997 | Muijs Van De Moer et al. | |
| 5,626,599 | A | 5/1997 | Bourne et al. | |
| 5,634,936 | A | 6/1997 | Linden et al. | 606/213 |
| 5,649,950 | A | 7/1997 | Bourne et al. | |
| 5,649,959 | A | 7/1997 | Hannam et al. | |
| 5,663,063 | A | 9/1997 | Peoples et al. | |
| 5,683,411 | A | 11/1997 | Kavteladze et al. | 606/200 |
| 5,690,674 | A | 11/1997 | Diaz | |
| 5,693,085 | A | 12/1997 | Buirge et al. | |
| 5,702,421 | A | 12/1997 | Schneidt | 606/213 |
| 5,709,707 | A | 1/1998 | Lock et al. | 606/213 |
| 5,717,259 | A | 2/1998 | Schexnayder | |
| 5,720,754 | A | 2/1998 | Middleman et al. | 606/127 |
| 5,725,552 | A | 3/1998 | Kotula et al. | 606/213 |
| 5,733,294 | A | 3/1998 | Forber et al. | 606/151 |
| 5,733,337 | A | 3/1998 | Carr, Jr. et al. | |
| 5,741,297 | A * | 4/1998 | Simon | 606/213 |
| 5,776,162 | A | 7/1998 | Kleshinski | 606/198 |
| 5,776,183 | A | 7/1998 | Kanesaka et al. | |
| 5,797,960 | A | 8/1998 | Stevens et al. | 606/213 |
| 5,800,516 | A | 9/1998 | Fine et al. | |
| 5,810,884 | A | 9/1998 | Kim | 606/213 |
| 5,823,956 | A | 10/1998 | Roth et al. | 600/374 |
| 5,829,447 | A | 11/1998 | Stevens et al. | 128/898 |
| 5,853,420 | A | 12/1998 | Chevillon et al. | |
| 5,853,422 | A | 12/1998 | Huebsch et al. | |
| 5,855,614 | A | 1/1999 | Stevens et al. | 623/11 |
| 5,861,003 | A | 1/1999 | Latson et al. | |
| 5,865,791 | A | 2/1999 | Whayne et al. | |
| 5,879,366 | A | 3/1999 | Shaw et al. | 606/213 |
| 5,893,856 | A | 4/1999 | Jacob et al. | 606/151 |
| 5,902,319 | A | 5/1999 | Daley | 606/219 |
| 5,904,703 | A | 5/1999 | Gilson | 606/213 |
| 5,919,200 | A | 7/1999 | Stambaugh et al. | 606/159 |
| 5,924,424 | A | 7/1999 | Stevens et al. | 128/898 |
| 5,928,250 | A | 7/1999 | Koike et al. | |
| 5,944,738 | A | 8/1999 | Amplatz et al. | 606/213 |
| 5,955,110 | A | 9/1999 | Patel et al. | |
| 5,976,174 | A | 11/1999 | Ruiz | 606/213 |
| 5,989,268 | A | 11/1999 | Pugsley, Jr. et al. | 606/144 |
| 5,993,475 | A | 11/1999 | Lin et al. | 606/213 |
| 5,993,844 | A | 11/1999 | Abraham et al. | |
| 5,997,575 | A | 12/1999 | Whitson et al. | |
| 6,010,517 | A | 1/2000 | Baccaro | 606/151 |
| 6,024,756 | A * | 2/2000 | Huebsch et al. | 606/213 |
| 6,030,007 | A | 2/2000 | Bassily et al. | |
| 6,056,760 | A | 5/2000 | Koike et al. | 606/148 |
| 6,071,998 | A | 6/2000 | Muller et al. | |
| 6,077,291 | A | 6/2000 | Das | 606/213 |
| 6,077,880 | A | 6/2000 | Castillo et al. | |
| 6,079,414 | A | 6/2000 | Roth | 128/898 |
| 6,080,182 | A | 6/2000 | Shaw et al. | 606/213 |
| 6,096,347 | A | 8/2000 | Geddes et al. | |
| 6,106,913 | A | 8/2000 | Scardino et al. | |
| 6,113,609 | A | 9/2000 | Adams | |
| 6,117,159 | A | 9/2000 | Huebsch et al. | 606/213 |
| 6,126,686 | A | 10/2000 | Badylak et al. | |
| 6,132,438 | A | 10/2000 | Fleischman et al. | 606/139 |
| 6,143,037 | A | 11/2000 | Goldstein et al. | |
| 6,152,144 | A | 11/2000 | Lesh et al. | |
| 6,165,183 | A | 12/2000 | Kuehn et al. | 606/139 |
| 6,165,204 | A | 12/2000 | Levinson et al. | 606/232 |
| 6,171,329 | B1 | 1/2001 | Shaw et al. | 606/213 |
| 6,174,322 | B1 | 1/2001 | Schneidt | 606/213 |
| 6,174,330 | B1 | 1/2001 | Stinson | |
| 6,187,039 | B1 | 2/2001 | Hiles et al. | |
| 6,190,353 | B1 | 2/2001 | Makower et al. | |
| 6,206,895 | B1 | 3/2001 | Levinson | 606/144 |
| 6,206,907 | B1 | 3/2001 | Marino et al. | 606/215 |
| 6,214,029 | B1 | 4/2001 | Thill et al. | |
| 6,217,590 | B1 | 4/2001 | Levinson | 606/142 |
| 6,221,092 | B1 | 4/2001 | Koike et al. | 606/213 |
| 6,227,139 | B1 | 5/2001 | Nguyen et al. | |
| 6,228,097 | B1 | 5/2001 | Levinson et al. | 606/142 |
| 6,231,561 | B1 | 5/2001 | Frazier et al. | |
| 6,245,080 | B1 | 6/2001 | Levinson | 606/144 |
| 6,245,537 | B1 | 6/2001 | Williams et al. | |
| 6,261,309 | B1 | 7/2001 | Urbanski | |
| 6,265,333 | B1 | 7/2001 | Dzenis et al. | |
| 6,270,515 | B1 | 8/2001 | Linden et al. | 606/213 |
| 6,277,138 | B1 | 8/2001 | Levinson et al. | 606/200 |
| 6,277,139 | B1 | 8/2001 | Levinson et al. | 606/200 |
| 6,287,317 | B1 | 9/2001 | Makower et al. | 606/153 |
| 6,290,674 | B1 | 9/2001 | Roue et al. | 604/107 |

| Patent No. | Date | Name | Class |
|---|---|---|---|
| 6,306,150 B1 | 10/2001 | Levinson | 606/158 |
| 6,306,424 B1 | 10/2001 | Vyakarnam et al. | |
| 6,312,446 B1 | 11/2001 | Huebsch et al. | 606/213 |
| 6,316,262 B1 | 11/2001 | Huisman et al. | |
| 6,319,263 B1 | 11/2001 | Levinson | 606/144 |
| 6,322,548 B1 | 11/2001 | Payne et al. | |
| 6,328,727 B1 | 12/2001 | Frazier et al. | |
| 6,334,872 B1 | 1/2002 | Termin et al. | |
| 6,342,064 B1 | 1/2002 | Koike et al. | 606/213 |
| 6,344,048 B1 | 2/2002 | Chin et al. | |
| 6,344,049 B1 | 2/2002 | Levinson et al. | 606/200 |
| 6,346,074 B1 | 2/2002 | Roth | |
| 6,348,041 B1 | 2/2002 | Klint | 600/585 |
| 6,352,552 B1 | 3/2002 | Levinson et al. | 623/1.15 |
| 6,355,052 B1 | 3/2002 | Neuss et al. | 606/213 |
| 6,356,782 B1 | 3/2002 | Sirimanne et al. | |
| 6,364,853 B1 | 4/2002 | French et al. | 604/35 |
| 6,371,904 B1 | 4/2002 | Sirimanne et al. | |
| 6,375,625 B1 | 4/2002 | French et al. | 600/573 |
| 6,375,671 B1 | 4/2002 | Kobayashi et al. | 606/213 |
| 6,379,342 B1 | 4/2002 | Levinson | 604/310 |
| 6,379,368 B1 | 4/2002 | Corcoran et al. | 606/153 |
| 6,387,104 B1 | 5/2002 | Pugsley, Jr. et al. | 606/139 |
| 6,398,796 B2 | 6/2002 | Levinson | 606/144 |
| 6,402,772 B1 | 6/2002 | Amplatz et al. | |
| 6,419,669 B1 | 7/2002 | Frazier et al. | |
| 6,426,145 B1 | 7/2002 | Moroni | |
| 6,436,088 B2 | 8/2002 | Frazier et al. | |
| 6,440,152 B1 | 8/2002 | Gainor et al. | 606/213 |
| 6,460,749 B1 | 10/2002 | Levinson et al. | 227/180.1 |
| 6,482,224 B1 | 11/2002 | Michler et al. | |
| 6,488,706 B1 | 12/2002 | Solymar | 623/3.1 |
| 6,494,888 B1 | 12/2002 | Laufer et al. | 606/153 |
| 6,508,828 B1 | 1/2003 | Akerfeldt et al. | |
| 6,514,515 B1 | 2/2003 | Williams | |
| 6,548,569 B1 | 4/2003 | Williams et al. | |
| 6,551,303 B1 | 4/2003 | Van Tassel et al. | |
| 6,551,344 B2 | 4/2003 | Thill | |
| 6,585,755 B2 | 7/2003 | Jackson et al. | |
| 6,596,013 B2 | 7/2003 | Yang et al. | |
| 6,599,448 B1 | 7/2003 | Ehrhard, Jr. et al. | |
| 6,610,764 B1 | 8/2003 | Martin et al. | |
| 6,623,508 B2 | 9/2003 | Shaw et al. | |
| 6,623,518 B2 | 9/2003 | Thompson et al. | |
| 6,626,936 B2 | 9/2003 | Stinson | |
| 6,629,901 B2 | 10/2003 | Huang | |
| 6,666,861 B1 | 12/2003 | Grabek | |
| 6,669,722 B2 | 12/2003 | Chen et al. | |
| 6,689,589 B2 | 2/2004 | Huisman et al. | |
| 6,712,804 B2 | 3/2004 | Roue et al. | |
| 6,712,836 B1 | 3/2004 | Berg et al. | |
| 6,726,696 B1 | 4/2004 | Houser et al. | |
| 6,828,357 B1 | 12/2004 | Martin et al. | |
| 6,838,493 B2 | 1/2005 | Williams et al. | |
| 6,867,247 B2 | 3/2005 | Williams et al. | |
| 6,867,248 B1 | 3/2005 | Martin et al. | |
| 6,867,249 B2 | 3/2005 | Lee | |
| 6,921,410 B2 | 7/2005 | Porter | |
| 7,097,653 B2 * | 8/2006 | Freudenthal et al. | 606/213 |
| 2001/0010481 A1 | 8/2001 | Blanc et al. | |
| 2001/0014800 A1 | 8/2001 | Frazier et al. | |
| 2001/0034537 A1 | 10/2001 | Shaw et al. | 606/213 |
| 2001/0034567 A1 | 10/2001 | Allen et al. | |
| 2001/0037129 A1 | 11/2001 | Thill | 606/213 |
| 2001/0039435 A1 | 11/2001 | Roue et al. | |
| 2001/0041914 A1 | 11/2001 | Frazier et al. | |
| 2001/0041915 A1 | 11/2001 | Roue et al. | |
| 2001/0044639 A1 | 11/2001 | Levinson | 606/228 |
| 2001/0049492 A1 | 12/2001 | Frazier et al. | 604/104 |
| 2002/0010481 A1 | 1/2002 | Jayaraman | 606/151 |
| 2002/0019648 A1 | 2/2002 | Akerfeldt et al. | |
| 2002/0026208 A1 | 2/2002 | Roe et al. | |
| 2002/0029048 A1 | 3/2002 | Miller | 606/138 |
| 2002/0032459 A1 | 3/2002 | Horzewski et al. | |
| 2002/0032462 A1 | 3/2002 | Houser et al. | 606/213 |
| 2002/0034259 A1 | 3/2002 | Tada | |
| 2002/0035374 A1 | 3/2002 | Borillo et al. | |
| 2002/0043307 A1 | 4/2002 | Ishida et al. | 148/411 |
| 2002/0052572 A1 | 5/2002 | Franco et al. | |
| 2002/0058989 A1 | 5/2002 | Chen et al. | |
| 2002/0077555 A1 | 6/2002 | Schwartz | 600/486 |
| 2002/0095174 A1 | 7/2002 | Tsugita et al. | |
| 2002/0096183 A1 | 7/2002 | Stevens et al. | |
| 2002/0099389 A1 | 7/2002 | Michler et al. | 606/139 |
| 2002/0107531 A1 | 8/2002 | Schreck et al. | |
| 2002/0111537 A1 | 8/2002 | Taylor et al. | |
| 2002/0111637 A1 | 8/2002 | Kaplan et al. | |
| 2002/0111647 A1 | 8/2002 | Khairkhahan et al. | |
| 2002/0120323 A1 | 8/2002 | Thompson et al. | |
| 2002/0128680 A1 | 9/2002 | Pavlovic | |
| 2002/0129819 A1 | 9/2002 | Feldman et al. | 128/831 |
| 2002/0164729 A1 | 11/2002 | Skraly et al. | |
| 2002/0169377 A1 | 11/2002 | Khairkhahan et al. | |
| 2002/0183786 A1 | 12/2002 | Girton | 606/213 |
| 2002/0183787 A1 | 12/2002 | Wahr et al. | 606/213 |
| 2002/0183823 A1 | 12/2002 | Pappu | |
| 2002/0198563 A1 | 12/2002 | Gainor et al. | |
| 2003/0004533 A1 | 1/2003 | Dieck et al. | |
| 2003/0023266 A1 | 1/2003 | Welch et al. | |
| 2003/0028213 A1 | 2/2003 | Thill et al. | |
| 2003/0045893 A1 | 3/2003 | Ginn | |
| 2003/0050665 A1 | 3/2003 | Ginn | |
| 2003/0055455 A1 | 3/2003 | Yang et al. | |
| 2003/0057156 A1 | 3/2003 | Peterson et al. | |
| 2003/0059640 A1 | 3/2003 | Marton et al. | |
| 2003/0065379 A1 | 4/2003 | Babbas et al. | |
| 2003/0100920 A1 | 5/2003 | Akin et al. | |
| 2003/0120337 A1 | 6/2003 | Van Tassel et al. | |
| 2003/0139819 A1 | 7/2003 | Beer et al. | |
| 2003/0171774 A1 | 9/2003 | Freudenthal et al. | |
| 2003/0191495 A1 | 10/2003 | Ryan et al. | |
| 2003/0195530 A1 | 10/2003 | Thill | |
| 2003/0204203 A1 | 10/2003 | Khalrkhahan et al. | |
| 2004/0044361 A1 | 3/2004 | Franzier et al. | |
| 2004/0073242 A1 | 4/2004 | Chanduszko | |
| 2004/0176799 A1 | 9/2004 | Chanduszko et al. | |
| 2004/0210301 A1 | 10/2004 | Obermiller | |
| 2004/0234567 A1 | 11/2004 | Dawson | |
| 2005/0025809 A1 | 2/2005 | Hasirci et al. | |
| 2005/0043759 A1 | 2/2005 | Chanduszko | |
| 2005/0113868 A1 | 5/2005 | Devellian | |
| 2005/0267523 A1 | 12/2005 | Devellian et al. | |
| 2005/0273135 A1 | 12/2005 | Chanduszko et al. | |
| 2005/0288786 A1 | 12/2005 | Chanduszko | |
| 2006/0122647 A1 | 6/2006 | Callaghan et al. | |
| 2006/0265004 A1 | 11/2006 | Callaghan et al. | |
| 2007/0010851 A1 | 1/2007 | Chanduszko et al. | |
| 2007/0167981 A1 | 7/2007 | Opolski | |

FOREIGN PATENT DOCUMENTS

| | | |
|---|---|---|
| EP | 0362113 | 4/1990 |
| EP | 0474887 A1 | 3/1992 |
| EP | 0 839 549 | 5/1998 |
| EP | 1 013 227 | 6/2000 |
| EP | 1 046 375 | 10/2000 |
| EP | 1 222 897 | 7/2002 |
| WO | WO 96/25179 | 8/1996 |
| WO | WO 96/31157 | 10/1996 |
| WO | WO-98/07375 A1 | 2/1998 |
| WO | WO-98/08462 | 3/1998 |
| WO | WO-98/16174 | 4/1998 |
| WO | WO-98/18864 | 5/1998 |
| WO | WO-98/29026 A2 | 7/1998 |
| WO | WO-98/51812 | 11/1998 |
| WO | WO-99/05977 A1 | 2/1999 |

| | | |
|---|---|---|
| WO | WO-99/18862 A1 | 4/1999 |
| WO | WO-99/18864 | 4/1999 |
| WO | WO-99/18870 A1 | 4/1999 |
| WO | WO-99/18871 A1 | 4/1999 |
| WO | WO-99/30640 A1 | 6/1999 |
| WO | WO 00/27292 | 5/2000 |
| WO | WO 00/44428 | 8/2000 |
| WO | WO-01/21247 A1 | 3/2001 |
| WO | WO-01/30268 A1 | 5/2001 |
| WO | WO 01/49185 | 7/2001 |
| WO | WO-01/78596 A1 | 10/2001 |
| WO | WO-02/17809 A1 | 3/2002 |
| WO | WO 02/24106 | 3/2002 |
| WO | WO-03/024337 A1 | 3/2003 |
| WO | WO-03/053493 A1 | 7/2003 |
| WO | WO-03/059152 | 7/2003 |
| WO | WO-03/063732 A | 8/2003 |
| WO | WO 03/077733 | 9/2003 |
| WO | WO-03/082076 | 10/2003 |
| WO | WO-03/103476 A2 | 12/2003 |
| WO | WO-2004/032993 | 4/2004 |
| WO | WO-2004/037333 | 5/2004 |
| WO | WO-2004/043266 | 5/2004 |
| WO | WO-2004/043508 | 5/2004 |
| WO | WO-2004/052213 | 6/2004 |
| WO | WO-2005/006990 | 1/2005 |
| WO | WO-2005/018728 | 3/2005 |
| WO | WO-2005/027752 | 3/2005 |
| WO | WO-2005/074813 | 8/2005 |
| WO | WO-2005/092203 | 10/2005 |
| WO | WO-2005/110240 | 11/2005 |
| WO | WO-2005/112779 | 12/2005 |
| WO | WO-2006/036837 | 4/2006 |
| WO | WO-2006/102213 | 9/2006 |

OTHER PUBLICATIONS

Kimura, A., et al., "Effects of Neutron Irradiation on the Transformation Behavior in Ti-Ni Alloys," Abstract, Proceedings of the Int'l Conf. On Mariensitic Transformations (1992) pp. 935-940.
Ramanathan, G., et al., "Experimental and Computational Methods for Shape Memory Alloys," 15th ASCE Engineering Mechanics Conf., Jun. 2-5, 2003.
Shabalovskaya, S., "Surface, corrosion and biocompatibility aspects of Nitinol as an implant material," Bio-Medical materials and Engineering, (2002) vol. 12, pp. 69-109.
Uchil, J. "Shape Memory Alloys—Characterization Techniques," Pramana—Journal of Physics, (2002) vol. 58, Nos. 5 & 6, pp. 1131-1139.
Stöckel, "Nitinol Medical Devices and Implants," SMST-2000 Conference Proceedings, 2001, pp. 531-541.
SMST-2000, "Proceedings of the International Conference on Shape Memory and Superelastic Technologies," Apr. 30 to May 4, 2000, Asilomar Conference Center.
Ruiz et al. "The Puncture Technique: A New Method for Transcatheter Closure of Patent Foramen Ovale," Catheterization and Cardiovascular Interventions 53, Wiley-Liss, Inc., 2001, pp. 369-372.
International Search Report, International Application No. PCT/US03/17390, mailed on Oct. 6, 2003, 4 pgs.
Athanasion, T., "Coronary Artery Bypass with the Use of a Magnetic Distal Anastomotic Device: Surgical Technique and Preliminary Experience," The Heart Surgery Forum #2004-1024, 2004, 4 pgs.
Bachthaler, M. et al., "Corrosion of Tungsten Coils After Peripheral Vascular Embolization Theraphy: Influence on Outcome and Tungsten Load", *Catherization and Cardiovascular Interventions*, vol. 62, pp. 380-384, 2004.
European Examination Report, European Application No. 04781644.2, mailed Aug. 23, 2007 (3 Pages).
Falk, V., "Facilitated Endoscopic Beating Heart Coronary Artery Bypass Grafting Using a Magnetic Coupling Device," Journal of Thoracic and Cardiovascular Surgery, vol. 126,(5), pp. 1575-1579.
Filsoufi, F., et al., "Automated Distal Coronary Bypass with a Novel Magnetic Coupler (MVP system)," J. Thoracic and Cardiovascular Surgery, vol. 127(1), pp. 185-192.
International Search Report for International Patent Application No. PCT/AU03/00759, filed Jun. 19, 2003. (4 pgs).
International Search Report, International Application No. PCT/US02/40850 mailed Jun. 19, 2003 (4 pgs).
International Search Report, International Application No. PCT/US03/01050, mailed Jul. 8, 2003 (1 pg).
International Search Report, International Application No. PCT/US03/09051, mailed Sep. 29, 2003 (2 pgs).
International Search Report, International Application No. PCT/US03/17715, mailed Mar. 24, 2004 (2 pgs).
International Search Report, International Application No. PCT/US03/32133, mailed Apr. 22, 2004 (1 pg).
International Search Report, International Application No. PCT/US03/34003 mailed Oct. 3, 2004 (4 pgs).
International Search Report, International Application No. PCT/US03/35479, mailed Apr. 14, 2004 (2 pgs).
International Search Report, International Application No. PCT/US03/35998 mailed Jun. 16, 2004 (5 pgs).
International Search Report, International Application No. PCT/US03/39253, mailed Apr. 19, 2004 (4 pgs).
International Search Report, International Application No. PCT/US04/022643, mailed Mar. 31, 2005 (2 pgs).
International Search Report, International Application No. PCT/US04/026998, mailed Apr. 22, 2005 (5 pgs).
International Search Report, International Application No. PCT/US04/029978, mailed Jan. 26, 2005 (3 pgs).
International Search Report, International Application No. PCT/US05/006703, mailed Jul. 25, 2005 (3 pgs).
International Search Report, International Application No. PCT/US05/013705 mailed Aug. 4, 2005 (4 pgs).
International Search Report, International Application No. PCT/US05/015382, mailed Oct. 6, 2005 (4 pgs).
International Search Report, International Application No. PCT/US05/34276, mailed Oct. 9, 2007. (1 pg).
International Search Report, International Application No. PCT/US06/009978, mailed Jul. 13, 2006 (2 pgs).
International Search Report, International Application No. PCT/US07/065546, mailed Oct. 29, 2007. 4 pages.
International Search Report, International Application No. PCT/US2007/065526, mailed Aug. 8, 2007 (5 pgs).
International Search Report, International Application No. PCT/US2007/065541, mailed Aug. 7, 2007 (4 pgs).
International Search Report, International Application No. PCT/US97/14822, mailed Feb. 20, 1998 (2 pgs).
International Search Report, International Application No. PCT/US97/17927, mailed Feb. 10, 1998 (1 pg).
Isotalo, T. et al., "Biocompatibility Testing of a New Bioabsorbable X-Ray Positive SR-PLA 96/4 Urethral Stent", *The Journal of Urology*, vol. 163, pp. 1764-1767, Nov. 1999.
Klima, U., "Magnetic Vascular Port in Minimally Invasive Direct Coronary Artery Bypass Grafting," Circulation, 2004, II-55-II-60.
Meier, MD, Bernhard et al., "Contemporary Management of Patent Foramen Ovale," American Heart Association, Inc., Circulation, 2003, vol. 107, pp. 5-9.
Parviainen, M. et al., "A New Biodegradable Stent for the Pancreaticojejunal Anastomosis After Pancreaticoduodenal Resection: In Vitro Examination and Pilot Experiences in Humans", *Pancreas*, vol. 21, No. 1, pp. 14-21, 2000.
Ruddy, A.C. et al., "Rheological, Mechanical and Thermal Behaviour of Radipaque Filled Polymers", *Polymer Processing Research Centre, School of Chemical Engineering, Queen's University of Belfast*, 5 pages.
Vaajanen, A. et al., "Expansion and Fixation Properties of a New Braided Biodegradable Urethral Stent: An Experimental Study in the Rabbit", *The Journal of Urology*, vol. 169, pp. 1771-1174, Mar. 2003.

* cited by examiner

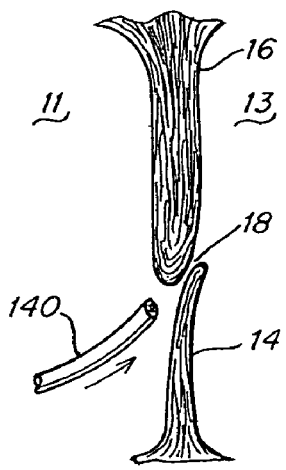
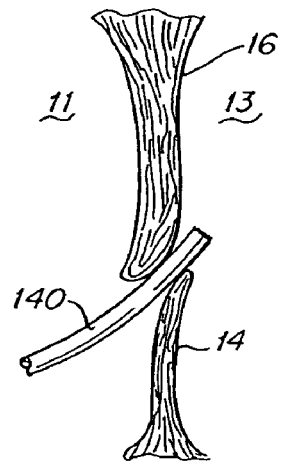
Fig. 14A          Fig. 14B
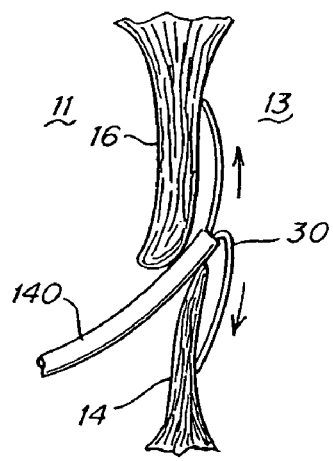
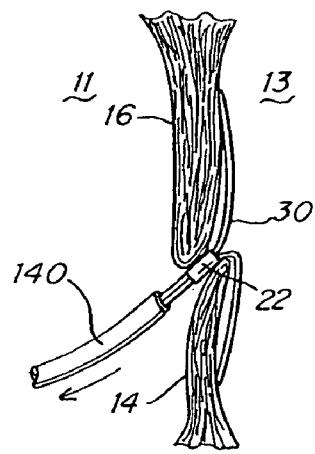
Fig. 14C          Fig. 14D
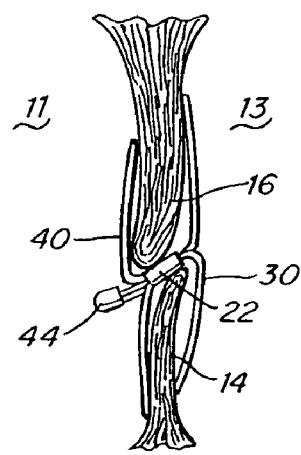
Fig. 14E

PATENT FORAMEN OVALE (PFO) CLOSURE DEVICE WITH RADIAL AND CIRCUMFERENTIAL SUPPORT

FIELD OF THE INVENTION

The present invention relates generally to an occlusion device for the closure of physical anomalies like septal apertures, such as patent foramen ovale and other septal and vascular defects.

BACKGROUND OF THE INVENTION

A patent foramen ovale (PFO), illustrated in FIG. 1, is a persistent, one-way, usually flap-like opening in the wall between the right atrium 11 and left atrium 13 of the heart 10. Because left atrial (LA) pressure is normally higher than right atrial (RA) pressure, the flap usually stays closed. Under certain conditions, however, right atrial pressure can exceed left atrial pressure, creating the possibility that blood could pass from the right atrium 11 to the left atrium 13 and blood clots could enter the systemic circulation. It is desirable that this circumstance be eliminated.

The foramen ovale serves a desired purpose when a fetus is gestating in utero. Because blood is oxygenated through the umbilical chord, and not through the developing lungs, the circulatory system of a heart in a fetus allows the blood to flow through the foramen ovale as a physiologic conduit for right-to-left shunting. After birth, with the establishment of pulmonary circulation, the increased left atrial blood flow and pressure results in functional closure of the foramen ovale. This functional closure is subsequently followed by anatomical closure of the two over-lapping layers of tissue: septum primum 14 and septum secundum 16. However, a PFO has been shown to persist in a number of adults.

The presence of a PFO is generally considered to have no therapeutic consequence in otherwise healthy adults. Paradoxical embolism via a PFO is considered in the diagnosis for patients who have suffered a stroke or transient ischemic attack (TIA) in the presence of a PFO and without another cause of ischemic stroke. While there is currently no definitive proof for a cause-effect relationship, many studies have confirmed a strong association between the presence of a PFO and the risk for paradoxical embolism or stroke. In addition, there is significant evidence that patients with PFO who have had a cerebral vascular event are at increased risk for future, recurrent cerebrovascular events.

Accordingly, patients with an increased future risk are considered for prophylactic medical therapy to reduce the risk of a recurrent embolic event. These patients are commonly treated with oral anticoagulants, which have the potential for adverse side effects, such as hemorrhaging, hematoma, and interactions with a variety of other drugs. The use of these drugs can alter a person's recovery and necessitate adjustments in a person's daily living pattern.

In certain cases, such as when anticoagulation is contraindicated, surgery may be necessary or desirable to close the PFO. The surgery would typically include suturing a PFO closed by attaching septum secundum to septum primum. This sutured attachment can be accomplished with either an interrupted or a continuous stitch and is a common way a surgeon shuts a PFO under direct visualization.

Umbrella devices and a variety of other similar mechanical closure designs, developed initially for percutaneous closure of atrial septal defects (ASDs), have been used in some instances to close PFOs. These devices have the potential to allow patients to avoid the potential side effects often associated with anticoagulation therapies and the risks of invasive surgery. However, umbrella devices and the like that are designed for ASDs are not optimally suited for use as a PFO closure device.

Currently available designs of septal closure devices present drawbacks, including technically complex implantation procedures. Additionally, there are not insignificant complications due to thrombus, fractures of the components, conduction system disturbances, perforations of heart tissue, and residual leaks. Many devices have high septal profile and may include large masses of foreign material, which may lead to unfavorable body adaptation of a device. Since ASD devices are designed to occlude a hole, many lack anatomic conformability to the PFO flap-like anatomy. That is, when inserting an ASD device to close a PFO, the narrow opening and the thin flap may form impediments to proper deployment. Even if an occlusive seal is formed, the device may be deployed in the heart on an angle, which could leave some components not securely seated against the septum, thereby risking thrombus formation due to hemodynamic disturbances. Finally, some septal closure devices are complex to manufacture, which may result in lack of consistency in product performance.

The present invention is designed to address these and other deficiencies of the prior art septal closure devices.

SUMMARY OF THE INVENTION

The present invention provides a device for occluding an anatomical aperture, such as a septal defect or a PFO. This occluder includes two sides connected by an intermediate joint. Each of the sides includes at least one wire or other elongate element for structural support (referred to collectively as "wire"), which is arranged to form non-overlapping loops. Each loop has at least one radially-extending segment that is adjacent to a radially-extending segment of another loop. In at least some embodiments, at least one pair of adjacent radially-extending segments is connected. The loops of the device may be of various shapes and sizes. In at least some embodiments, the loops have rounded peripheries. The configuration of the loops and sides of the occluder are varied according to different embodiments of the invention. In some embodiments, at least one of the sides includes a tissue scaffold.

The wires forming the occluders of the present invention may be constructed of various biocompatible materials. In some embodiments, the wires are formed of shape memory materials, e.g. nitinol. In other embodiments, the wires are formed of polymers, bioabsorbable polymers, or combinations thereof.

The occluder according to the present invention is designed such that, when deployed in vivo, the two sides are disposed on opposite sides of the septal tissue surrounding the aperture, i.e. septum primum and septum secundum. Thus, the two sides exert a compressive force on the septal tissue that is distributed along both the outer periphery of the occluder and the radially-extending segments. In at least some embodiments, the radially-extending segments increase the stiffness of the occluder, thereby preventing the occluder from becoming dislodged from its intended delivery site. In at least some embodiments, the flexible, rounded peripheries of the loops prevent the occluder from inflicting trauma upon the septal tissue as the heart contracts. In at least some embodiments of the present invention, the occluder is repositionable and/or retrievable. These and other advantageous features of the present invention will be explained in more detail in connection with the following illustrations.

BRIEF DESCRIPTION OF THE DRAWINGS

FIGS. 14A-14E are side elevational views of one method for delivering an occluder according to the present invention to a septal defect;

DETAILED DESCRIPTION OF THE INVENTION

The present invention provides a device for occluding an aperture within body tissue. In particular and as described in detail below, the occluder of the present invention may be used for closing a PFO in the atrial septum of a heart. Although the embodiments of the invention are described with reference to a PFO, one skilled in the art will recognize that the device and method of the present invention may be used to treat other anatomical conditions. As such, the invention should not be considered limited to any particular anatomical condition.

Figure 1:
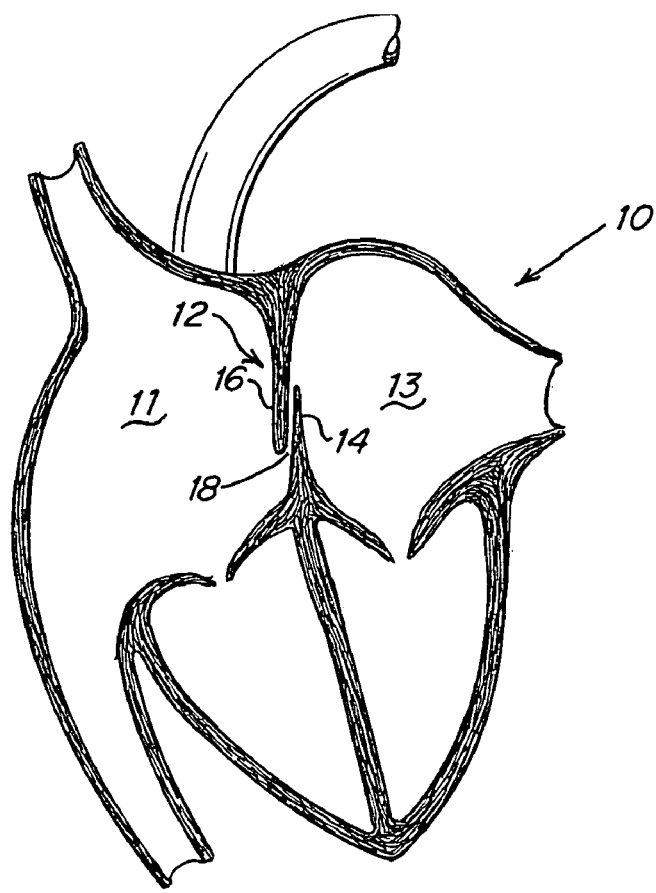
FIG. 1 is a schematic representation of a human heart including a septal defect.

FIG. 1 illustrates a human heart 10, having a right atrium 11 and a left atrium 13. The atrial septum 12 includes septum primum 14, septum secundum 16, and a passage 18 between the right 11 and left 13 atria. The anatomy of the septum varies widely within the population. In some people, septum primum 14 extends to and overlaps with septum secundum 16. The septum primum 14 may be quite thin. When a PFO is present, there is a chance that blood could travel through the passage 18 between septum primum 14 and septum secundum 16 (referred to as "the PFO tunnel").

Figure 2:
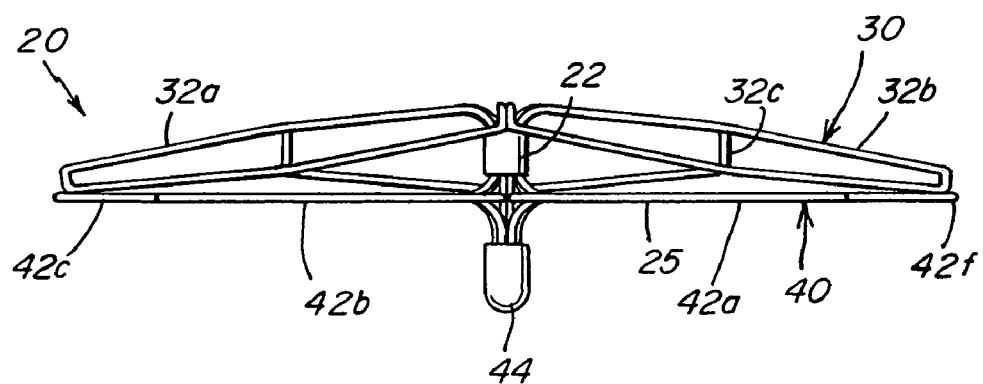
FIG. 2 is a top view of an occluder according to one embodiment of the invention.
Figure 3:
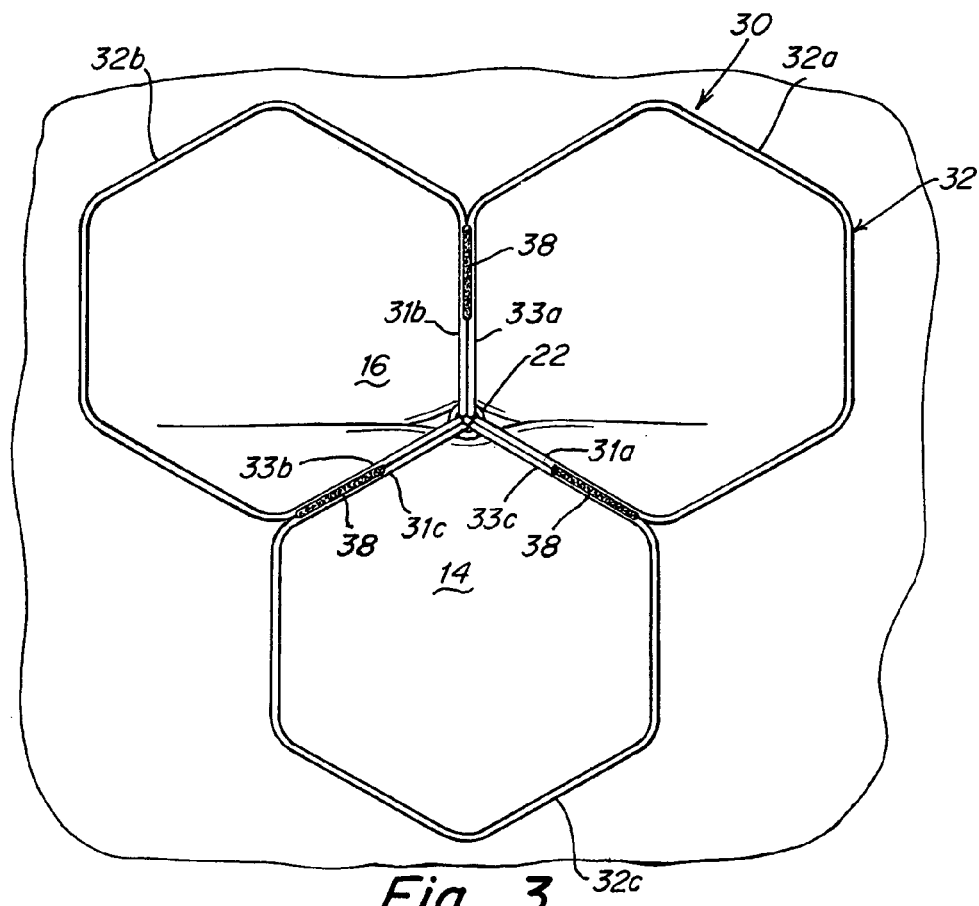
FIG. 3 is a front elevational view of the distal side of the occluder of FIG. 2.
Figure 4:
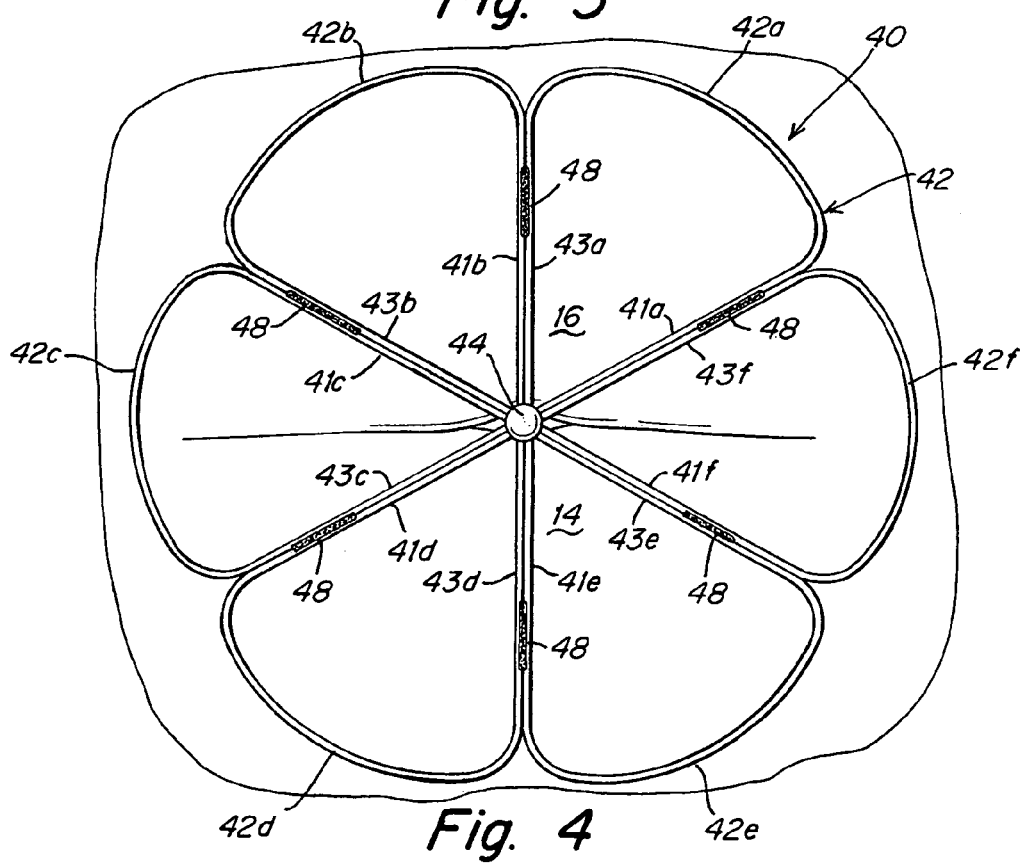
FIG. 4 is a front elevational view of the proximal side of the occluder of FIG. 2.
Figures 6A, 6B:
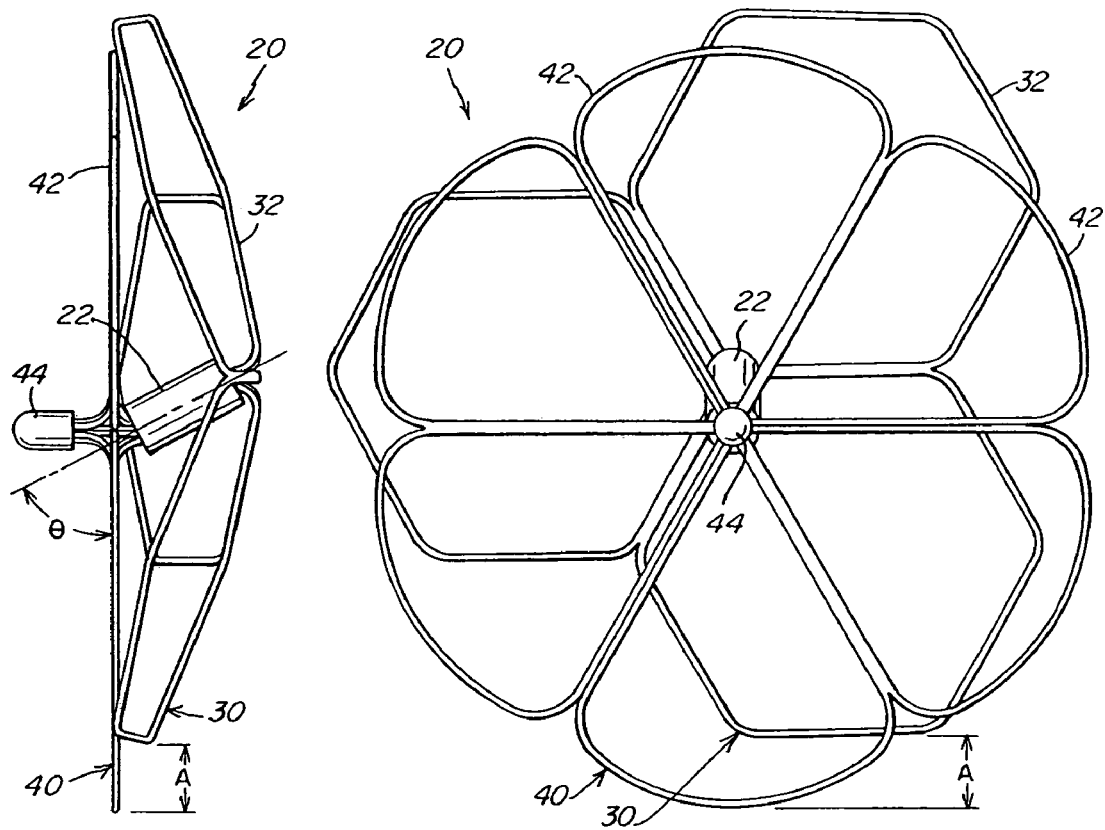
FIGS. 6A and 6B are a side view and a front elevational view, respectively, of an occluder according to another embodiment of the present invention.
Figure 7:
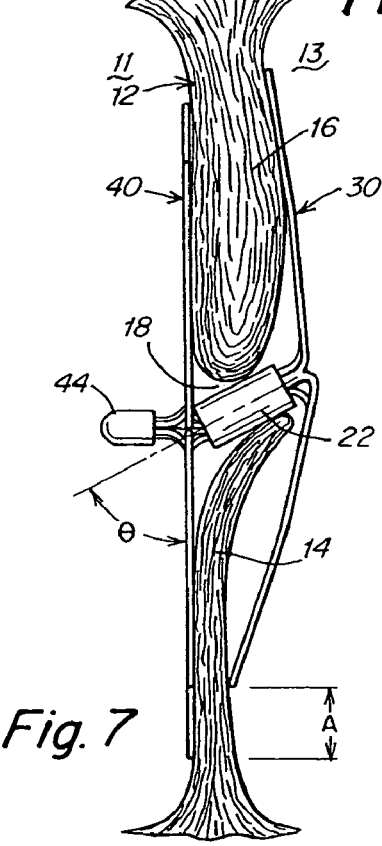
FIG. 7 is a side elevational view of the occluder of FIGS. 6A and 6B deployed in vivo.

An occluder according to one embodiment of the present invention is shown in FIGS. 2 through 7. As shown in FIG. 2, the occluder 20 includes a distal side 30 (FIG. 3) and a proximal side 40 (FIG. 4). In this application, "distal" refers to the direction away from a catheter insertion location and "proximal" refers to the direction nearer the insertion location. Distal side 30 and proximal side 40 are connected by intermediate joint 22. As shown in FIG. 7, the occluder 20 may be inserted into the septal tissue 12 to prevent the flow of blood through the passage 18, i.e. the occluder may extend through the PFO tunnel 18 such that the distal side 30 is located in the left atrium 13 and the proximal side 40 is located in the right atrium 11. Various features of the occluder 20 will be described with reference to FIGS. 2 through 7.

The occluder 20 is constructed of wire or other elongate element for structural support, referred to collectively as "wire" 25. The wire is arranged to form loops in both the distal 30 and proximal 40 sides of the occluder 20. According to some embodiments of the present invention, several wires 25 are used to construct the occluder 20. According to other embodiments, the occluder may be formed of a tube using, for example, an etching or cutting process to create elongate members. The elongate members have the general structure of a wire, i.e. long and thin, but are not necessarily round. As used herein, the term "wire" is intended to encompass wires and elongate members (whether or not formed by an etched tube).

The wire(s) 25 may be formed of various biocompatible materials. In at least some embodiments, the occluder 20 is formed of shape memory material (e.g. nitinol). The thermal shape memory and/or superelastic properties of shape memory materials, e.g. nitinol, permit the occluder 20 to resume and maintain its intended shape in vivo despite being distorted during the delivery process. In particular embodiments, the occluder 20 is formed of nitinol that is austenitic at body temperature. Alternatively, or additionally, the occluder 20 may be formed of other high-strength super-alloys, such as Hastelloy® (available from Haynes International), Elgiloy®, or MP35N. In still other embodiments, occluder 20 may be formed of a polymer (e.g. plastics), bioabsorbable polymer, or combination of the foregoing.

The distal side 30 of the occluder 20 (also called the "anchor portion") is shown in FIG. 3. The distal side 30 includes three loops 32a, 32b, and 32c, collectively referred to as loops 32. As illustrated, the loops 32 are evenly distributed about and held together at center joint 22. Each of loops 32 has six sides of roughly the same linear dimension. Each of loops 32 has at least one segment that is adjacent to a segment of another of loops 32. Specifically, segment 33a of loop 32a is adjacent to segment 31b of loop 32b; segment 33b of loop 32b is adjacent to segment 31c of loop 32c; and segment 33c of loop 32c is adjacent to segment 31a of loop 32a.

Although the distal side 30 of the occluder 20 shown in FIG. 3 includes three loops 32, occluders according to the present invention may include any number of loops 32 necessary for a given application. Occluders having less than or equal to ten loops 32 may be formed without requiring significant adjustments. In general, the stiffness of the occluder 20 increases as the number of loops 32 increases. However, occluders having more than ten loops 32 may be complicated to manufacture and deliver through the vasculature. Whatever the number of loops chosen, the loops 32 may be of varied sizes to facilitate delivery, e.g. to improve collapsibility of the occluder 20 or to enhance securement at the delivery site. For example, loops 32 sized to better conform with anatomical landmarks will provide enhanced securement of the occluder 20 to the septal tissue 12 in vivo.

Regardless of the number of loops included in distal side 30, the outer shape of the loops 32 may vary. For example, as illustrated in FIG. 3, the loops 32 may be hexagonal with 120 degree angles at their bends (ie. "blunt loops"). Alternatively, or additionally, the non-adjacent wire segments may be rounded to provide for a smoother perimeter. As the number of loops 32 in the distal side 30 of occluder 20 increases, it becomes desirable to round the outer perimeters of the loops 32 so as to prevent the infliction of trauma on the surrounding septal tissue 12. The loops 32 may also be formed as concave structures, such that the outermost portions of the loops 32 of the distal side 30 oppose the outermost portions of the loops 42 of the proximal side 40, as described in more detail below, thereby creating a desirable opposing force that secures the occluder 20 at its desired location in vivo.

As previously mentioned, the wires 25 forming loops 32 are attached at center joint 22. The adjacent segments extend radially outward from center joint 22 at a spacing of approximately 120 degrees apart. The area of septal tissue enclosed by loops 32 provides support for the distal side 30 once the occluder 20 is deployed in vivo. In at least one embodiment of the present invention, a connection is provided between the adjacent segments, e.g. between segments 33*a* and 31*b*, between segments 33*b* and 31*c*, and between segments 33*c* and 31*a*. For example, as shown in FIG. 3, the adjacent segments may be connected by welds 38. Such connections provide additional stiffness to the occluder 20 and help secure the occluder 20 at its desired location in vivo, as described in more detail below.

The adjacent segments may be connected in a variety of ways. As previously indicated, the adjacent segments may be welded. The length of the welds 38 may extend along less than the entire radial distance of the adjacent segments. Alternatively, the adjacent segments may be connected with a tube, e.g. a hypo tube, having a smaller diameter than the diameter of the coupled adjacent segments. In such a configuration, the tube holds the segments together by exerting a compressive force against the wires. Numerous additional means of connecting the segments will be apparent to those skilled in the art, e.g. glue, clips, sutures, polymer sleeves, etc., and are considered to be within the scope of the present invention.

As previously indicated, the connections, e.g. welds 38, between adjacent segments provide stiffness to the distal side 30 of the occluder 20. As illustrated in FIG. 3, the welds 38 may extend a significant distance along the length of the adjacent segments or may extend along only a portion of the adjacent segments. Without connections between the adjacent segments, a force on any of loops 32 will be borne by that loop alone, and the stiffness of the distal side 30 is diminished. The capacity to vary the stiffness of the distal side 30 using various numbers and types of connections provides significant advantages. Thus, for some applications of the present invention, it may be desirable to include connections between some adjacent segments but not others or to vary the radial distance that the connections extend and/or the placement of the connections relative to the center joint 22. As the distance that the connections, e.g. welds 38, extend increases, the distal side 30 becomes stiffer. When the connections extend along less than half of the radial distance, the stiffness of the distal side 30 is diminished. The location of welds 38 also affects the stiffness of the occluder 50. For example, a shorter weld 38 placed at a more radially outward location along the adjacent segments will increase the stiffness and dislodgement resistance of the occluder 20. In at least some embodiments of the present invention, the connections, e.g. welds 38, extend along the entire length of the adjacent segments.

It should be noted that the inclusion of connections, e.g. welds 38, to increase the stiffness of the distal side 30 necessitates the use of a greater force to maintain the occluder 20 in reduced profile (i.e. in delivery configuration). The delivery system for an occluder 20 including distal side 30 having connections, e.g. welds 38, must, therefore, possess greater radial strength to contain such a configuration.

The proximal side 40 of the occluder 20 is shown in FIG. 4. The proximal side 40 includes six loops, 42*a*-42*f*, collectively referred to as loops 42. The loops 42 are evenly distributed about tip 44. Tip 44 may be a weld, solder, or tube into which the wires would fit. Each of loops 42 is formed of wire segments that extend radially outward from tip 44, bend approximately 180 degrees, and then extend back to intermediate joint 22. Thus, one end of each of loops 42 is attached to tip 44, while the other end of each of loops 42 is attached to intermediate joint 22. As a result, the axial position of each of loops 42 in proximal side 40 is slightly offset.

Figure 5:
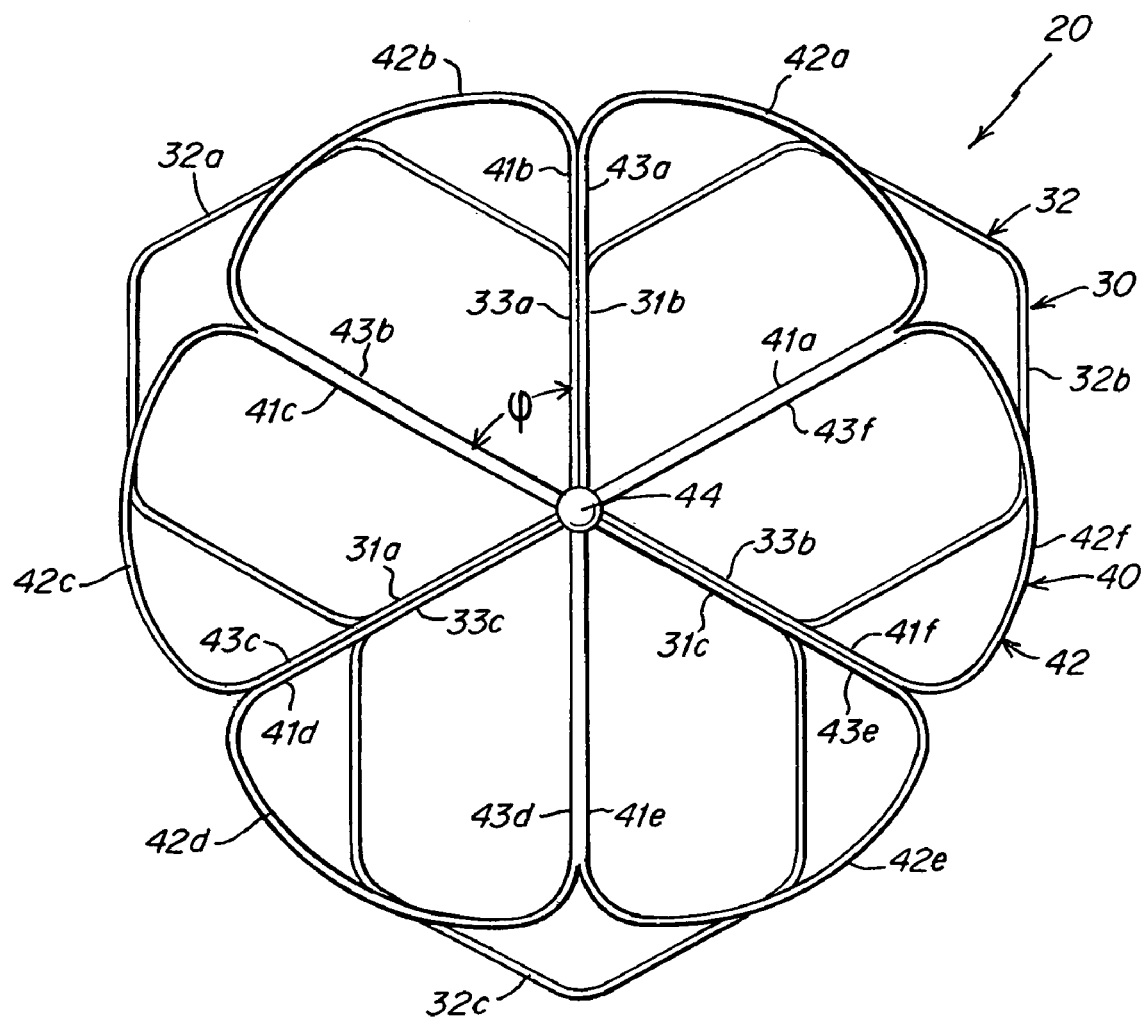
FIG. 5 is a front elevational view of the occluder of FIG. 2.

The wires forming each of loops 42 do not overlap, i.e. they are not intertwined or weaved. In at least one embodiment, illustrated in FIG. 5, the radially-extending segments of the proximal side 40 are rotated, for example, 60 degrees with respect to the radially-extending segments of the distal side 30. Thus, as shown in FIG. 5, the proximal radially-extending segments 41*a*, 43*b*, 41*c*, 43*d*, 41*e*, and 43*f*, which depart from intermediate joint 22 are rotated 60 degrees (as indicated by angle φ) with respect to distal radially-extending segments 31*a*, 33*a*, 31*b*, 33*b*, 31*c*, and 33*c*. Further, the loops 42 of proximal side 40 may be flat, while the loops 32 of distal side 30 may be concave, as previously described. Upon deployment in vivo, the opposing compressive forces exerted by the sides 30 and 40 on the septal tissue 12 are particularly advantageous.

Although the proximal side 40 of the occluder 20 shown in FIG. 4 includes six loops 42, one skilled in the art will recognize that the proximal side 40 of an occluder according to the present invention may include any number of loops 42 required for a given application. However, in view of the fact that the loops 42 are non-overlapping, it may not be practical to include more than ten loops 42 in proximal side 40.

Figure 9:
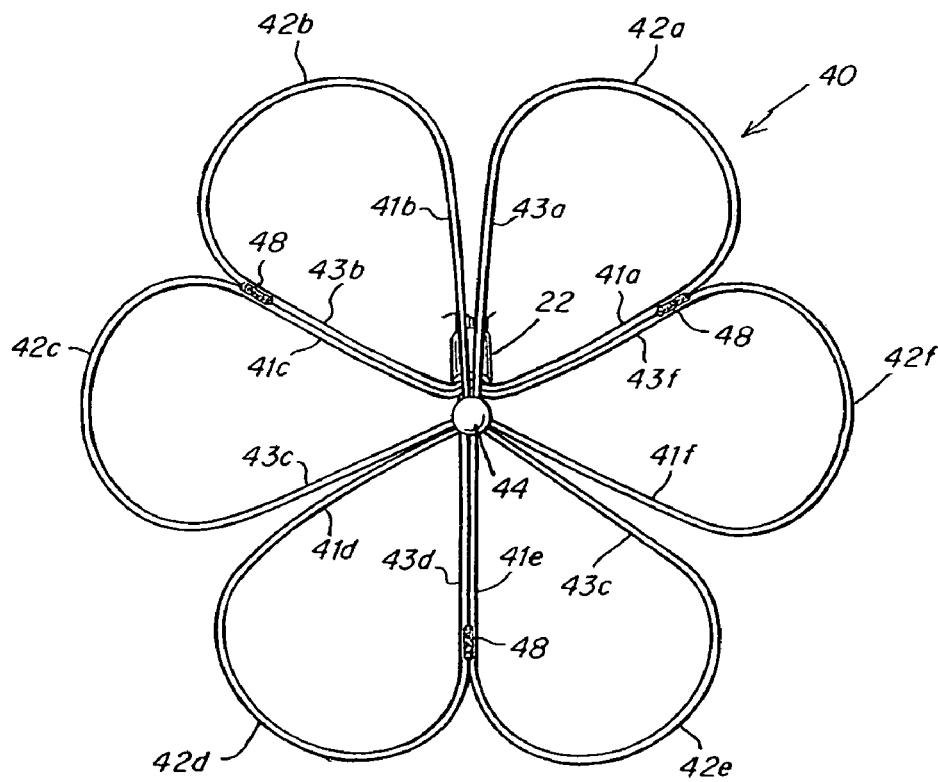
FIG. 9 is a front elevational view of the proximal side of an occluder according to still another embodiment of the present invention.

In a manner similar to that described above with regard to the distal side 30, loops 42 of proximal side 40 also include adjacent segments that may be connected. Specifically, segment 43*a* of loop 42*a* is adjacent to segment 41*b* of loop 42*b*; segment 43*b* of loop 42*b* is adjacent to segment 41*c* of loop 42*c*; segment 43*c* of loop 42*c* is adjacent to segment 41*d* of loop 42*d*; segment 43*d* of loop 42*d* is adjacent to segment 41*e* of loop 42*e*; segment 43*e* of loop 42*e* is adjacent to segment 41*f* of loop 42*f*; and segment 43*f* of loop 42*f* is adjacent to segment 41*a* of loop 42*a*. Connections may be included between any or all of the adjacent segments. The adjacent segments may be connected using any of the connection means previously described, e.g. welds 48. For example, as shown in FIG. 4, welds 48 are located between each pair of adjacent segments. Alternatively, as shown in FIG. 9, welds 98 are located between adjacent segments that are spaced 120 degrees apart, i.e. between segments 43*b* and 41*c*, between segments 43*d* and 41*e*, and between segments 43*f* and 41*a*. In preferred embodiments, welds are typically located on those adjacent segments extending from intermediate joint 22, such that the segments contacting the septal tissue 12 in the right atrium 11 are stiffest. Furthermore, including connections between at least those adjacent segments that contact the septal tissue minimizes fretting and the possibility of corrosion due to metal rubbing against metal.

As indicated previously and shown in FIG. 2, distal side 30 and proximal side 40 of occluder 20 are connected by intermediate joint 22. The intermediate joint 22 secures the wires of the device and, according to some embodiments, may be a weld, solder or tube. If a tube is used, the tube may have a diameter slightly less than that of the collected wires, such that the tube may be expanded during delivery and then returned to its reduced diameter following deployment of the occluder 20 in vivo. The reduced diameter tube will secure the wires forming loops 32 and 42 into the tube. A tube capable of expanding and reducing may be constructed of a shape memory material, e.g. nitinol. Alternatively, the intermediate joint 22 may be a tube having a diameter larger than that of the collected wires; following deployment of the occluder 20 in vivo, this tube may be crimped to secure the wires forming loops 32 and 42.

In other embodiments of the present invention, the intermediate joint 22 may be a spring, e.g. a coil spring. According to these embodiments, the spring is designed to pull the proximal side 40 of occluder 20 closer to the distal side 30, thereby compressing the septal tissue 12 between the distal 30 and proximal 40 sides in vivo. The tension of the spring may be selected such that the occluder 20 accommodates septal tissue of varying thicknesses. When considering the characteristics of the spring, the need to accommodate septal tissue of varying thicknesses and the need to provide sufficient (but not too much) compressive force must be balanced. One skilled in the art will be capable of selecting a spring meeting these criteria for a given application.

In still further embodiments of the present invention, intermediate joint 22 is positioned at an angle θ, as shown in FIG. 6. Often, anatomical anomalies have non-perpendicular apertures and are sometimes quite significantly non-perpendicular. Thus, the occluder 20 may include an angled intermediate joint 22, such that the angle of the anatomical aperture is more closely matched by the pre-formed angle θ of the occluder 20. Accordingly, the distal 30 and proximal 40 sides of occluder 20 are more likely to be seated against and minimize distortion to the septal tissue 12 surrounding the passage 18. A well-seated occluder 20 is less likely to permit blood leakage between the right 11 and left 13 atria, and the subject into which the occluder 20 has been placed is, therefore, less likely to suffer embolisms and other adverse events. Advantageously, angled intermediate joint 22 also facilitates delivery of occluder 20, as described in more detail below, because it is angled toward the end of the delivery catheter. In at least some embodiments, the angle θ is about 0-45 degrees off the plane created by the proximal side 40. One skilled in the art will recognize that the concept of an angled intermediate joint may also be applied to septal occluders other than those disclosed herein.

When intermediate joint 22 is positioned at angle θ, distal side 30 and proximal side 40 of occluder 20 may be configured such that they are either directly opposing or, as shown in FIGS. 6A and 6B, offset by distance A. One skilled in the art will, of course, recognize that the configuration of either or both of distal side 30 and proximal side 40 may be adjusted such that the compressive forces applied by the distal 30 and proximal 40 sides of occluder 20 are as directly opposing as possible. However, in some clinical applications, an occluder 20 having an offset of distance A may be particularly desirable. For example, as shown in FIG. 7, if the septal tissue 12 surrounding passage 18 includes a disproportionately thick portion (e.g. septum secundum 16 as compared to septum primum 14), the offset may be used to seat occluder 20 more securely upon septal tissue 12. Moreover, the offset A allows each of sides 30 and 40 to be centered around each side of an asymmetric defect.

When an intermediate joint 22 at angle θ is included in occluder 20, a marker is required to properly orient the occluder 20 in its intended in vivo delivery location. For example, platinum wire may be wrapped around one of loops 32 or 42 so as to permit visualization of the orientation of the occluder 20 using fluoroscopy. Alternatively, other types of markers may be used, e.g. coatings, clips, etc. As will be readily understood by one skilled in the art, the orientation of a non-symmetrical occluder 20 during delivery is of great importance. Of course, when a non-symmetrical occluder 20 is used, the periphery of the occluder 20 may be configured such that the clamping force applied by the proximal side 40 is directly opposed to that applied by the distal side 30.

Upon deployment in vivo (a process described in detail below), an occluder according to the present invention applies a compressive force to the overlapping layers of septal tissue 12, ie. septum primum 14 and septum secundum 16. Distal side 30 is seated against the septal tissue 12 in the left atrium 13; joint 22 extends through passage 18; and proximal side 40 is seated against the septal tissue 12 in the right atrium 11. As illustrated in FIGS. 2, 5, and 7, the proximal 40 and distal 30 sides of occluder 20 overlap significantly, such that septum primum 14 and septum secundum 16 are "sandwiched" between them once the occluder 20 is deployed. The connected, adjacent segments provide a radially-extending compressive force, while the peripheral loops 32 and 42 provide a circumferential compressive force. Thus, the compressive forces are more evenly and more widely distributed across the surface of the septal tissue 12 surrounding the PFO. The unique combination of radially-extending, connected, adjacent segments and peripheral loops 32 and 42, therefore, provides the occluder 20 with superior dislodgement resistance as compared to prior art devices. As used herein, "dislodgement resistance" refers to the ability of an occluder 20 to resist the tendency of the force applied by the unequal pressures between the right 11 and left 13 atria (i.e. the "dislodging force") to separate the occluder 20 from the septal tissue 12. Generally, a high dislodgement resistance is desirable.

Moreover, loops 32 and 42 are configured to provide occluder 20 with adequate surface area to seal the PFO. For example, the broad configuration of loops 32 and 42 increases the surface area of occluder 20. Thus, loops 32 and 42 provide sealing along a large circumference around the passage 18 (i.e. the PFO), thereby minimizing the possibility of leakage between the right 11 and left 13 atria.

While configured to provide sufficient circumferential sealing, loops 32 and 42 are also configured to minimize the trauma they inflict on the septal tissue 12 surrounding the PFO. Specifically, two features of loops 32 and 42 achieve this. First, the peripheries of loops 32 and 42 may be rounded. Second, the peripheries of loops 32 and 42 are formed of a single wire and are, therefore, more flexible than the interiorly-located, connected, adjacent segments, which are formed of two wires. These features minimize the overall trauma inflicted by occluder 20 on the septal tissue 12 surrounding the PFO. Accordingly, occluder 20 has a low compression resistance. As used herein, "compression resistance" refers to the ability of an occluder 20 to resist the lateral compressive force applied by the heart as it contracts during a heartbeat. Generally, an occluder that resists compressive force, i.e. has high compression resistance, is undesirable because its rigid configuration may cause trauma to the septal tissue 12, the right atrium 11, and/or the left atrium 13.

In heretofore known occluder designs, dislodgement resistance must usually be sacrificed in order to improve, i.e. minimize, compression resistance. However, the occluder 20 according to the present invention possesses both increased dislodgement resistance and minimized compression resistance. These desirable attributes are achieved by the unique combination of radially-extending, connected, adjacent segments and peripheral loops 32 and 42 discussed above. The radially-extending, connected, adjacent segments (i.e. struts) increase the stiffness and, correspondingly, the dislodgment resistance of the occluder 20. The atraumatic shape of the peripheral loops 32 and 42 decreases the compression resistance of the occluder 20. In effect, because the struts are formed of double-stranded wire and the peripheries of the loops 32 and 42 are formed of single-stranded wire, the center of the occluder 20 is twice as strong as its parameter. This, correspondingly, produces the advantageous combination of increased dislodgement resistance and minimized compression resistance in occluder 20.

Figure 8:
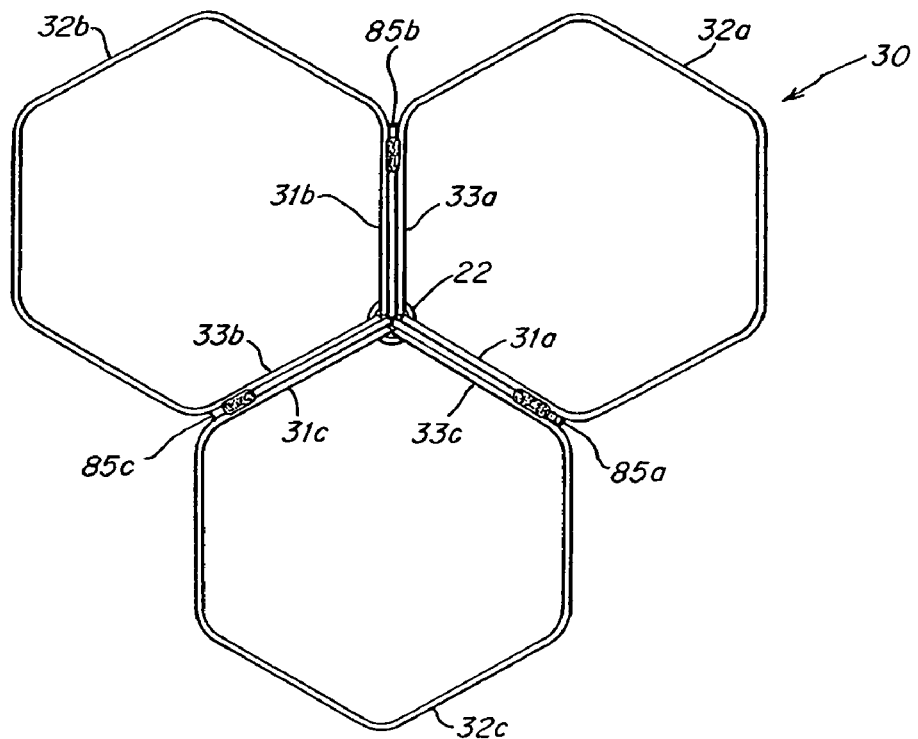
FIG. 8 is a front elevational view of the distal side of an occluder according to a further embodiment of the present invention.

The dislodgement resistance of occluder 20 may be further increased without increasing the compression resistance by the inclusion of additional struts. As illustrated in FIG. 8, additional struts 85a-85c, collectively referred to as additional struts 85, may be included between loops 32a-32c, i.e. between adjacent segments 33a and 31b, 33b and 31c, and 33c and 31a. Additional struts 85 may be of any suitable diameter, and, according to some embodiments, the diameter of additional struts 85 may vary along their length. For example, the diameter of additional struts 85 may increase as the additional struts 85 extend from intermediate joint 22 to the periphery of loops 32. Although FIG. 8 depicts additional struts 85 between loops 32 of distal side 30, additional struts 85 may additionally or alternatively be included between loops 42 of proximal side 40 of occluder 20.

The configuration of the occluder 20 according to the present invention provides several further advantages. First, broad loops 32 and 42 create a large surface area for occluder 20 and thereby anchor the occluder 20 more securely in vivo. In contrast, many previously known occluders include narrow loops, which afford less surface area for exertion of compressive forces and secure placement of the occluder 20. Second, the loops 32 and 42 create an occlusion perimeter that likely extends significantly beyond the passage 18. Third, loops 32 and 42 are non-overlapping, i.e. the wires are not intertwined or weaved. This non-overlapping configuration reduces the occurrence of fretting corrosion, which frequently occurs in prior art devices containing overlapping wires.

Occluder 20 may be modified in various ways. According to some embodiments of the present invention, loops 32 of distal side 30 and loops 42 of proximal side 40 may be formed in a variety of shapes. Four examples are illustrated in FIGS. 10A-10D. For convenience, only the proximal side 40 of each of these modified embodiments is depicted. However, the distal side 30 of occluder 20 may be similarly modified. The star-shaped pattern 100a shown in FIG. 10A includes four large loops, referred to collectively as loops 102a. Loops 102a are centered and approximately equally spaced around tip 44. Any or all of loops 102a may include a smaller loop, collectively referred to as loops 104a, at their radial extent. Smaller loops 104a may be capable of receiving a suture to facilitate retrieval of the occluder 20.

Figure 10A:
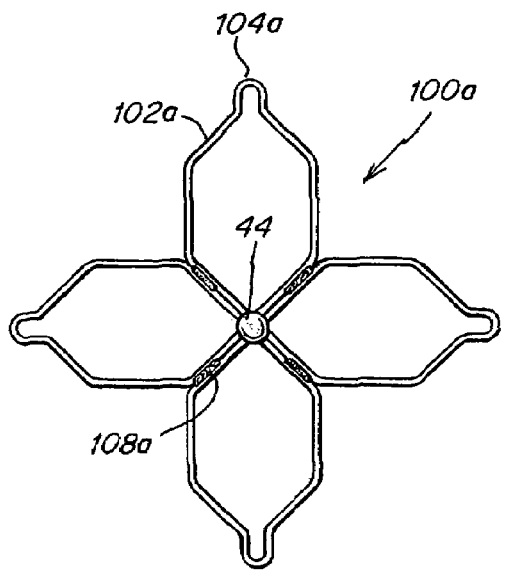
FIGS. 10A-10D are front elevational views of various embodiments of the proximal side of an occluder according to the present invention.
Figure 10B:
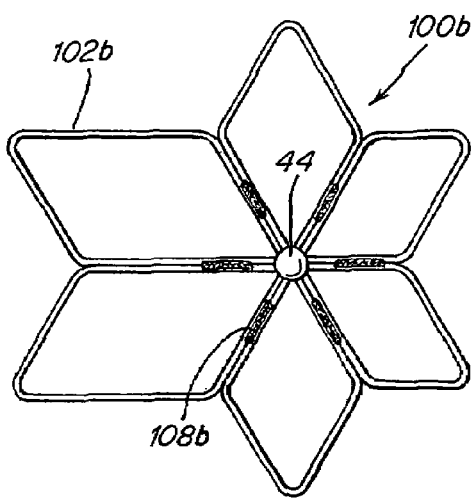

An alternative, diamond pattern 100b is shown in FIG. 10B. Diamond pattern 100b includes six diamond-shaped loops, referred to collectively as loops 102b, which are equally spaced around tip 44. Diamond pattern 100b is asymmetrically oriented, such that two of loops 102b extend further in the radial direction than the other loops 102b. This asymmetry may provide more complete and secure coverage of passage 18 than that provided by a symmetric occluder 20. The asymmetric pattern 100b may also facilitate the compact, percutaneous delivery of occluder 20.

Figure 10C:
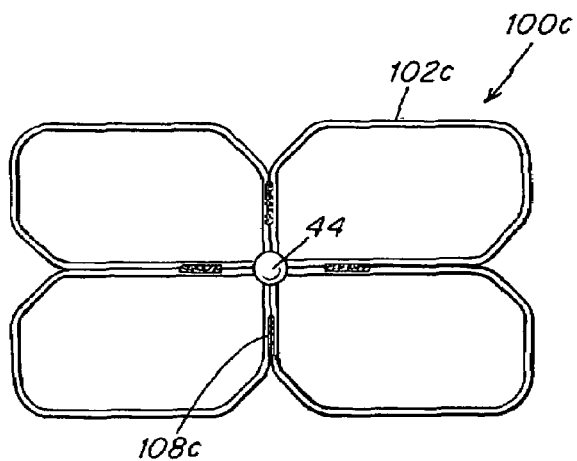

Still a further alternative, rectangular pattern 100c, is shown in FIG. 10C. Rectangular pattern 100c includes four rectangular-shaped loops, referred to collectively as loops 102c, which are equally spaced around tip 44. Rectangular pattern 100c provides extended coverage in two directions. Such a rectangular shape may be particularly suited for coverage of certain passages 18. Loops 102c may extend further in either the horizontal or vertical direction. As shown in FIG. 10C, loops 102c extend further in the horizontal direction.

Figure 10D:
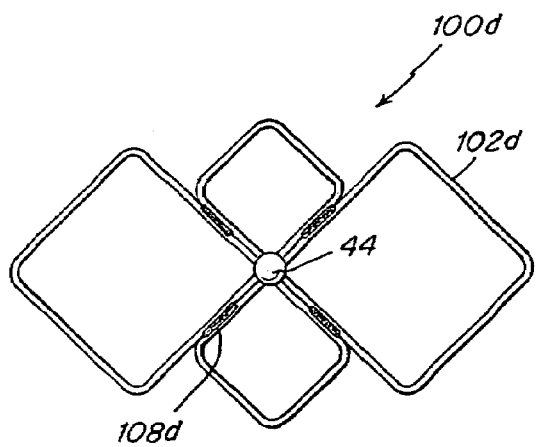

Yet a further alternative, diamond pattern 100d, is shown in FIG. 10D. Diamond pattern 100d includes four diamond-shaped loops, referred to collectively as loops 102d. Two of loops 102d are larger than the other two loops 102d. Thus, an extended amount of coverage may be provided across the passage 18 in either the horizontal or vertical direction. As shown in FIG. 10D, extended coverage is provided in the horizontal direction.

Of course, distal 30 and proximal 40 sides of occluder 20 may be configured in a combination of shapes and sizes depending on clinical needs presented by a given PFO. If required, the loops 102 in the illustrative patterns provided in FIGS. 10A-10D, may be rounded. The number of loops in embodiments of either the distal 30 or proximal 40 sides may be varied as necessary. As previously described, loops 102 in the illustrative patterns provided in FIGS. 10A-10D include adjacent segments, which may be connected by, e.g., welds 108a-108d, respectively. One skilled in the art will be able to identify the configuration(s) appropriate for a given clinical application.

Figure 11:
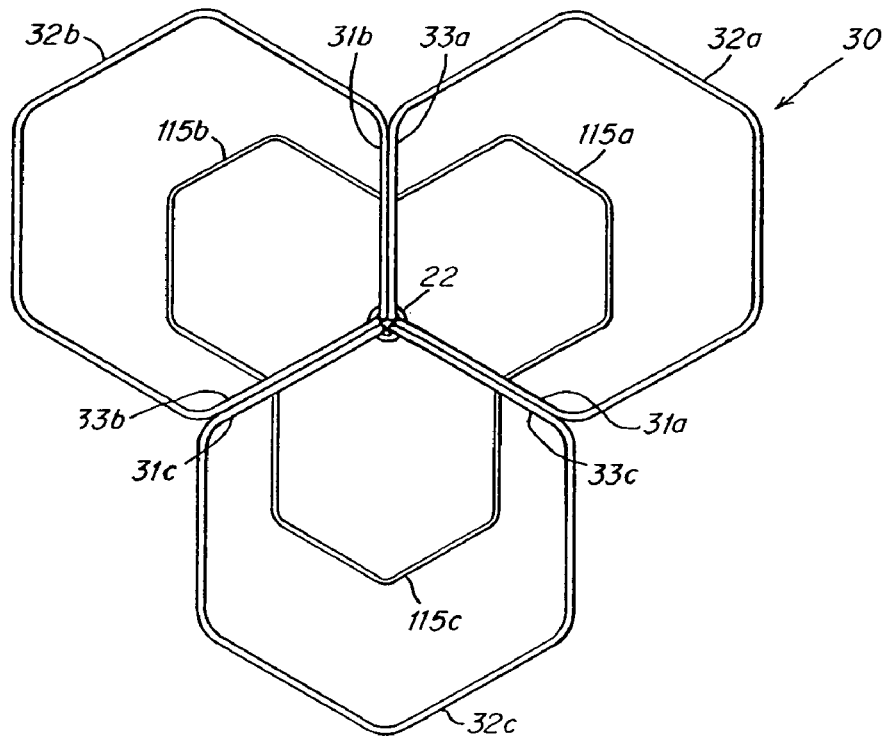
FIG. 11 is a front elevational view of the distal side of an occluder according to yet another embodiment of the present invention.

According to further embodiments of the present invention, smaller loops may be included on distal side 30 and/or proximal side 40 of occluder 20 to increase the compressive force applied in close proximity to passage 18 (i.e. the PFO). As illustrated in FIG. 11, three smaller loops 115a-115c, referred to collectively as smaller loops 115, are located on distal side 30. Smaller loops 115 are centered and equally spaced around intermediate joint 22. Although smaller loops 115a-115c in FIG. 11 correspond in number and alignment with loops 32a-32c, respectively, such correspondence is not required. Moreover, smaller loops 115 need not lie entirely in the same plane as loops 32 or 42. Thus, smaller loops 115 may bend in a direction generally perpendicular to the plane in which loops 32 or 42 lie. Smaller loops 115 may be attached only to intermediate joint 22 or, alternatively, may also be connected to the adjacent segments of loops 32. In still other embodiments, smaller loops 115 may be located at the peripheries of loops 32 rather than connected to intermediate joint 22. When the smaller loops 115 are located at the peripheries of loops 32, additional wire segments may be included within loops 32 to connect the smaller loops 115 to the intermediate joint 22. One skilled in the art will be able to determine the precise configuration of smaller loops 115 appropriate for a given clinical application.

Figure 12:
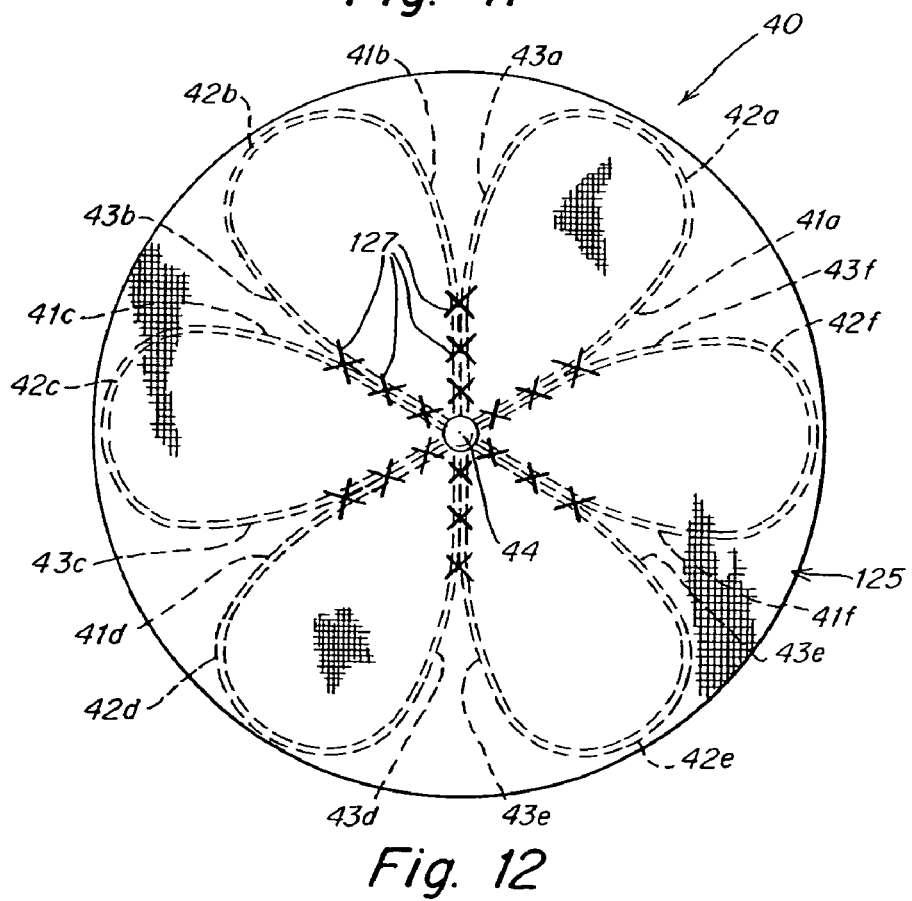
FIG. 12 is a front elevational view of a proximal side of an occluder according to the present invention that includes a tissue scaffold.

According to still further embodiments of the present invention and as illustrated in FIG. 12, distal side 30 and/or proximal 40 side of occluder 20 may include a tissue scaffold 125. Tissue scaffold 125 ensures more complete coverage of passage 18 and promotes encapsulation and endothelialization of septal tissue 12, thereby further encouraging anatomical closure of septum primum 14 and septum secundum 16. Tissue scaffold 125 may be formed of any flexible, biocompatible material capable of promoting tissue growth, including but not limited to polyester fabrics, Teflon-based materials, ePTFE, polyurethanes, metallic materials, polyvinyl alcohol (PVA), extracellular matrix (ECM) or other bioengineered material, synthetic bioabsorbable polymeric scaffolds, other natural materials (e.g. collagen), or combinations of the foregoing materials. For example, tissue scaffold 125 may be formed of a thin metallic film or foil, e.g. a nitinol film or foil, as described in U.S. patent appln. No. 2,003/0,059,640 (the entirety of which is incorporated herein by reference).

Adjacent segments may be stitched to tissue scaffold 125 so as to securely fasten the scaffold 125 to occluder 20. For example, FIG. 12 shows tissue scaffold 125 affixed to proximal side 40 of an occluder according to the present invention. Proximal side 40 includes six loops 42a-42f, collectively referred to as loops 42. Adjacent segments 43a and 41b, 43b and 41c, 43c and 41d, 43d and 41e, 43e and 41f, and 43f and 41a are attached to tissue scaffold 125 by stitches 127. Stitches 127 increase the stiffness of occluder 20 without welding or soldering. Additionally, when the adjacent segments of loops 42 are connected to tissue scaffold 125, the adjacent segments of loops 42 may be spaced apart a small distance (i.e. they need not necessarily be connected). Altering the spacing of the adjacent segments of loops 42 adjusts the stiffness of the occluder 20, which may be desirable in certain circumstances. One skilled in the art will be able to determine those clinical applications in which the use of stitches 127 and/or spaced, adjacent segments is appropriate.

Figure 13A:
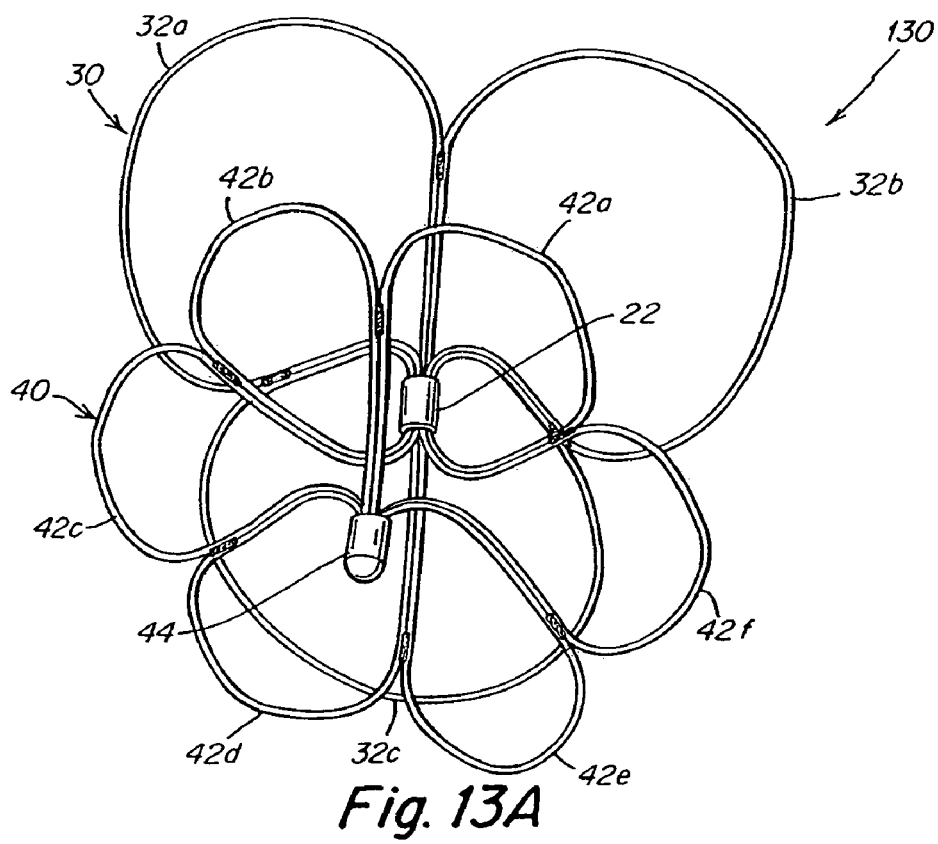
FIGS. 13A, 13B, and 13C are perspective, side elevational, and side elevation in vivo views, respectively, of an occluder according to yet a further embodiment of the present invention.
Figure 13B:
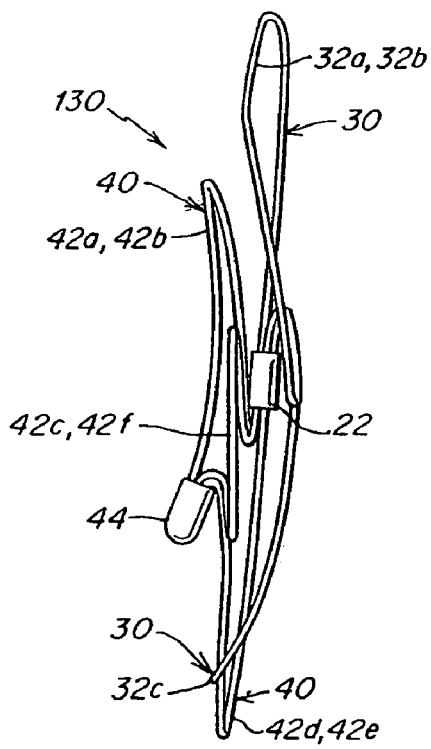
Figure 13C:
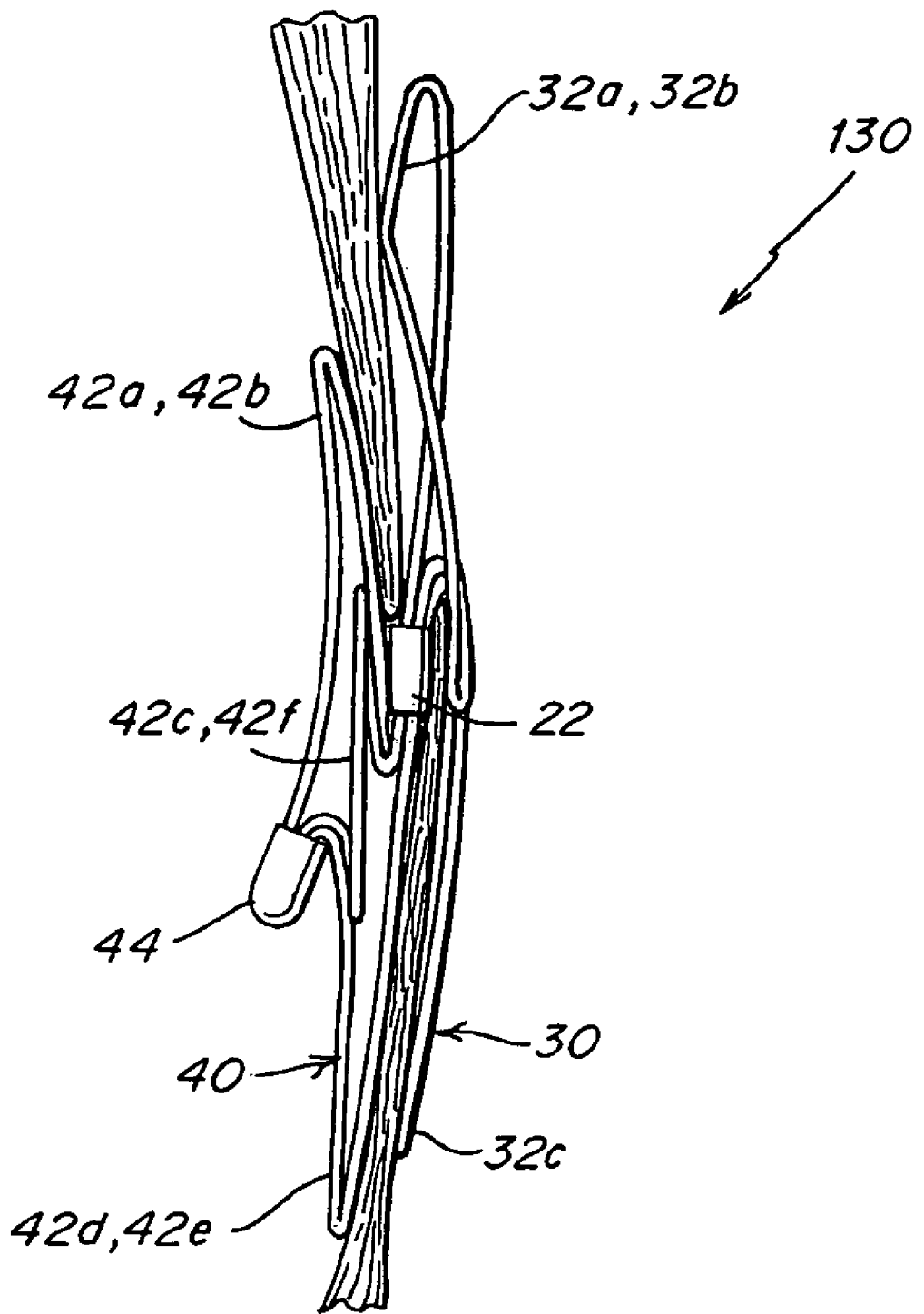

According to yet further embodiments of the present invention, the configuration of occluder 20 may be modified to produce the low-profile occluder 130 shown in FIG. 13A. In this embodiment, the manufacturing process is modified to increase the force with which the distal 30 and proximal 40 sides urge toward one another. Specifically, during manufacture, distal 30 and proximal 40 sides of occluder 20 may be crossed over each other (as shown in FIG. 13B) prior to connecting the adjacent segments of loops 32 and 42 (i.e. while the occluder 20 is in an "unconstrained" state). This crossed-over configuration may be achieved by, for example, using the shape memory properties of a shape memory material, such as nitinol, i.e. forcing, e.g., loops 42d and 42e of proximal side 40 through loop 32c of distal side 30 or vice versa and heat-setting the crossed-over shape. The crossed-over shape, therefore, becomes the predisposed position of occluder 20. Occluder 20 is then returned to its original, non-crossed-over state, and the adjacent segments of loops 32 and 42 are connected. The connected, adjacent segments prevent loops 42d and 42c from passing through loop 32c, and occluder 20 is, consequently, no longer capable of assuming its predisposed position. However, loops 42d and 42e of proximal side 42 still tend to bend toward distal side 30. The resulting occluder 130, shown in FIG. 13A, is of low profile. Further, occluder 130 exerts a greater compressive force on the septal tissue 12 when deployed in vivo (as shown in FIG. 13C) then at least some of the previously-described embodiments of occluder 20. This increased compressive force may be desirable in applications where the septal tissue 12 is particularly thin in one area, i.e. septum primum 14. The profile of occluder 130 may be lowered even further by angling tip 44 such that it is substantially parallel to proximal side 40 of occluder 130, as shown in FIG. 13A. Angled tip 44 also facilitates catheter delivery of occluder 130 because angled tip 44 points toward the end of the delivery catheter.

Finally, although occluders according to the present invention have been heretofore described as including distal 30 and proximal 40 sides having different configurations, an occluder 20 according to the present invention may, alternatively, include distal 30 and proximal 40 sides having identical configurations. This identical design may provide several advantages, including ease of manufacture. Furthermore, any of the configurations described herein for either distal side 30 or proximal side 40 may be applied to either or both of distal side 30 and proximal side 40 of occluder 20.

An occluder as described herein may be delivered to a septal defect using any of several suitable delivery techniques, two of which will be described herein. In the first delivery technique, shown in FIGS. 14A-14E, a delivery catheter 140 is used to deliver, e.g., occluder 20. Catheter 140 contains occluder 20 in its distorted, elongated form. As previously mentioned, in at least some embodiments, occluder 20 is formed of a shape memory material, e.g. nitinol, such that occluder 20 will resume its intended shape following deployment in vivo. As shown in FIG. 14A, delivery catheter 140 is first inserted into the right atrium 11 of the subject's heart. Catheter 140 is next inserted between septum primum 14 and septum secundum 16 (i.e. through passage 18, which, in this embodiment, is the PFO tunnel) and into the left atrium 13 (FIG. 14B). Distal side 30 of occluder 20 is then deployed into the left atrium 13, as shown in FIG. 14C. Following deployment of distal side 30, the catheter 140 is withdrawn through the PFO tunnel and into the right atrium 11, such that intermediate joint 22 is deployed through the PFO tunnel (FIG. 14D). Finally, proximal side 40 of occluder 20 is deployed into the right atrium 11, and catheter 140 is withdrawn from the heart (FIG. 14E). Once deployed, occluder 20 rests within the septal defect, and the distal 30 and proximal 40 sides exert a compressive force against septum primum 14 and septum secundum 16 in the left 13 and right 11 atria, respectively, to close the PFO.

Figure 15A:
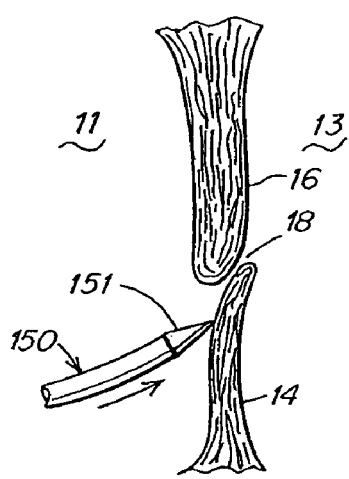
FIGS. 15A-15E are side elevational views of a second method for delivering an occluder according to the present invention to a septal defect.
Figure 15B:
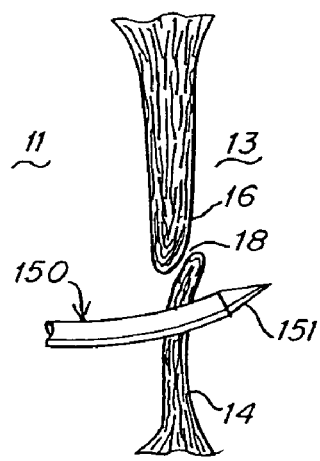
Figure 15C:
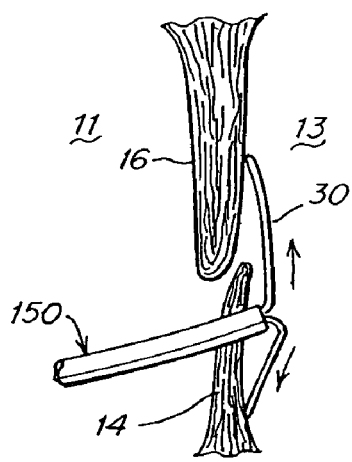
Figure 15D:
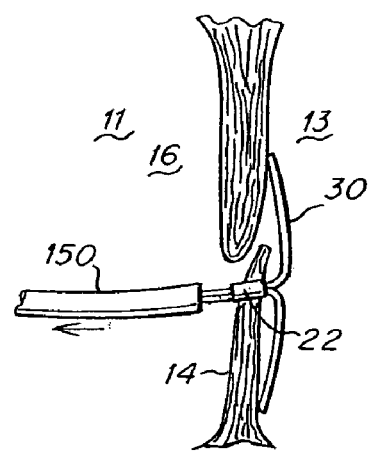
Figure 15E:
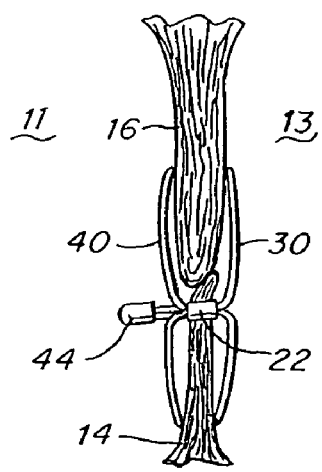

In a second delivery technique, shown in FIGS. 15A-15E, delivery catheter 150 includes a needle 151 capable of puncturing septum primum 14. As illustrated in FIG. 15A, septum primum 14 is long and thin and extends over septum secundum 16 in the left atrium 13. In some clinical applications, it may be advantageous to access the left atrium 13 by puncturing septum primum 14 rather than inserting the occluder 20 through the passage 18 between septum primum 14 and septum secundum 16. For example, some anatomical configurations include an extremely oblique passage 18 between the right atrium 11 and the left atrium 13. Thus, according to this second delivery technique, delivery catheter 150 includes a needle 151 on its distal end and contains occluder 20 in its distorted, elongated form. Catheter 150 is first inserted into the right atrium 11 of the subject's heart (FIG. 15A). Next, as shown in FIG. 15B, needle 151 punctures septum primum 14, and catheter 150 enters the left atrium 13. Needle 151 is then retracted, and distal side 30 of occluder 20 is deployed into the left atrium 13 (FIG. 15C). Following deployment of distal side 30, catheter 150 is withdrawn through septum primum 14 and into the right atrium 11, such that intermediate joint 22 is deployed through septum primum 14, as shown in FIG. 15D. Finally, proximal side 40 of occluder 20 is deployed into the right atrium 11, and catheter 150 is withdrawn from the heart (FIG. 15E). Once deployed, the distal 30 and proximal 40 sides of occluder 20 exert a compressive force against septum primum 14 and septum secundum 16 in the left 13 and right 11 atria, respectively, to close the PFO. When using this second delivery technique to deploy occluder 20, intermediate joint 22 should not be angled, i.e. intermediate joint 22 should be perpendicular to both the distal 30 and proximal 40 sides of the occluder 20.

Figure 16:
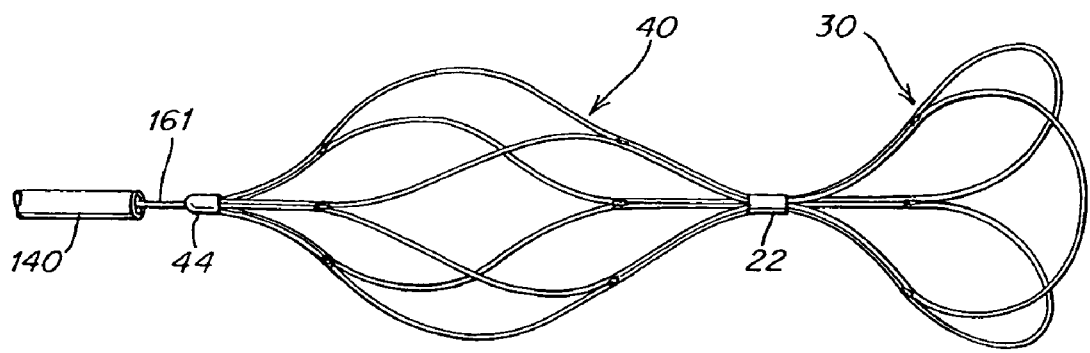
FIG. 16 is a side elevational view of a partially-deployed occluder according to the present invention.

FIG. 16 provides a more detailed representation of occluder 20 in its intermediate configuration between its compressed and fully-deployed states. As previously described, proximal side 40 of occluder 20 includes wire(s) 25, which form connected, adjacent radially-extending segments and loops 42, and tip 44. During delivery of occluder 20, tip 44 is attached to a delivery wire 161, in a manner known to those skilled in the art. When the proximal side 40 of occluder 20 is being deployed in the right atrium 11, the wire(s) 25 exit catheter 140 or 150 first, followed by tip 44, and, finally, delivery wire 161. Once occluder 20 has been positioned, delivery wire 161 is then fully retracted into the catheter 140 or 150 and the catheter is retracted out of the right atrium 11.

Figure 17A:
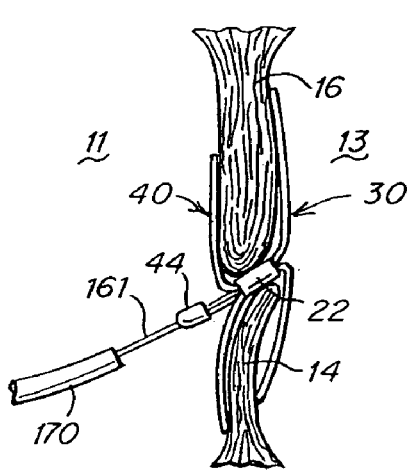
FIGS. 17A-17D are side elevational views of one method for retrieving an occluder according to the present invention from a septal defect.
Figure 17B:
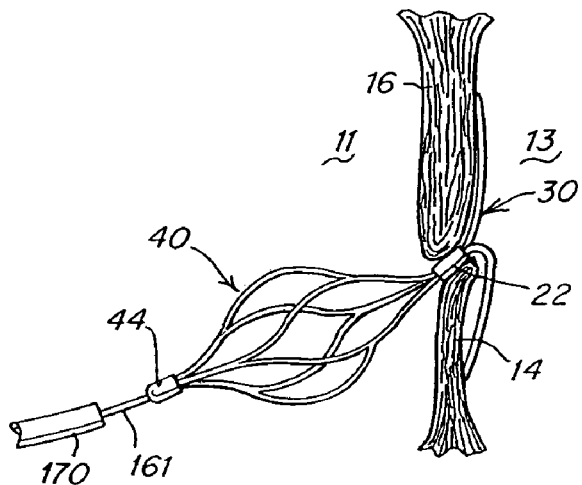
Figure 17C:
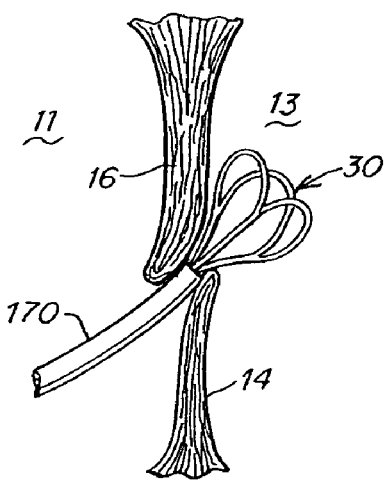
Figure 17D:
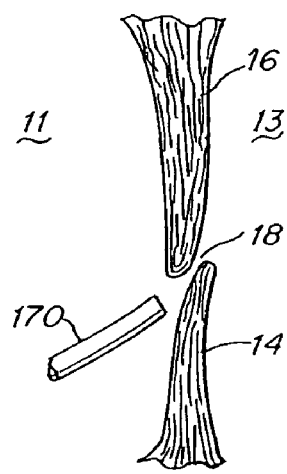

Delivery wire 161 may be used to reposition and/or retrieve occluder 20 as shown in FIGS. 17A-17D. If, following partial or complete deployment, the clinician desires to reposition or retrieve occluder 20, tip 44 may be recaptured with delivery wire 161 in catheter 170, as shown in FIG. 17A. As delivery wire 161 and tip 44 are pulled back into catheter 170, loops 42 of proximal side 40 fold back into their delivery (i.e. compressed) configuration (FIG. 17B) and are constrained by catheter 170. Catheter 170 is then advanced through passage 18 and delivery wire 161 is further retracted, such that loops 32 of distal side 30 fold into their delivery configuration (FIG. 17C) and are constrained by catheter 170. Catheter 170 containing retrieved occluder 20 is then withdrawn through passage 18, into the right atrium 11 (FIG. 17D), and out of the heart.

Figure 18:
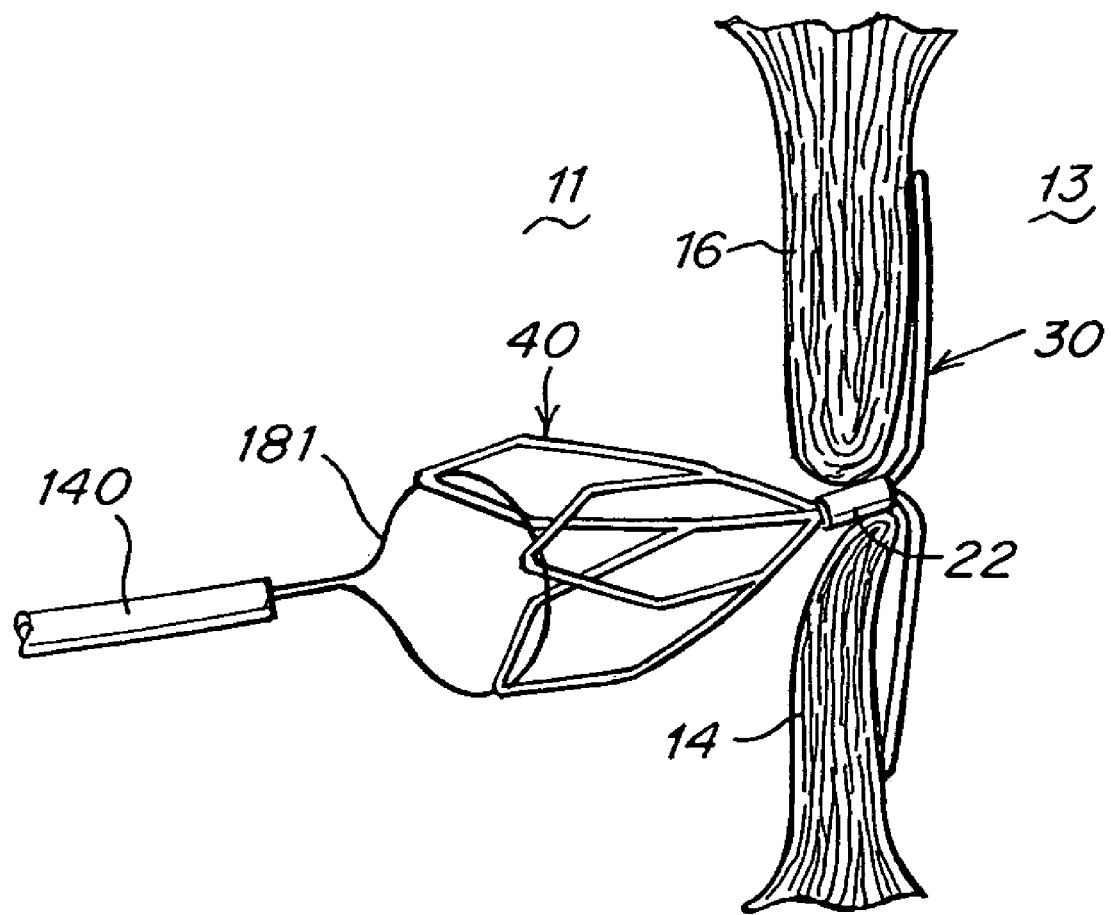
FIG. 18 is a side elevational view of a second method for retrieving an occluder according to the present invention from a septal defect.

In some embodiments according to the present invention, occluder 20 may be repositioned and/or retrieved using the alternative technique shown in FIG. 18. As previously described, an occluder 20 according to the present invention may include identical distal 30 and proximal 40 sides. Thus, for example, occluder 20 may include both distal 30 and proximal 40 sides as depicted in FIG. 3. In such an embodiment, proximal side 40 will not include a tip 44 for recovery by a delivery wire. An alternative method of retrieving the occluder is, therefore, required. In FIG. 18, occluder 20 has been delivered (according to either of the delivery techniques described above) to the extent that proximal side 40 has been deployed in the right atrium 11 but not released from catheter 140. A thread 181, such as a suture, is attached to each of loops 42 on proximal side 40 of occluder 20. If the occluder 20 requires repositioning, then thread 181 may be retracted and loops 42 will fold back into their delivery configuration, such that occluder 20 may be repositioned or, even, completely retrieved. Once occluder 20 has been deployed correctly, thread 181 may be cut and removed via catheter 140.

One skilled in the art would recognize that the occluders described herein may be used with anti-thrombogenic compounds, including but not limited to heparin and peptides, to reduce thrombogenicity of the occluder and/or to enhance the healing response of the septal tissue 12 following deployment of the occluder in vivo. Similarly, the occluders described herein may be used to deliver other drugs or pharmaceutical agents (e.g. growth factors, peptides). The anti-thrombogenic compounds, drugs, and/or pharmaceutical agents may be included in the occluders of the present invention in several ways, including by incorporation into the tissue scaffold 125, as previously described, or as a coating, e.g. a polymeric coating, on the wire(s) forming the distal 30 and proximal 40 sides of the occluder. Furthermore, the occluders described herein may include cells that have been seeded within tissue scaffold 125 or coated upon the wire(s) forming the distal 30 and proximal 40 sides of the occluder.

One skilled in the art would recognize that occluders according to this invention could be used in occluding other vascular and non-vascular openings. For example, the device could be inserted into a left atrial appendage or other tunnels or tubular openings within the body.

Having described preferred embodiments of the invention, it should be apparent that various modifications may be made without departing from the spirit and scope of the invention, which is defined in the claims below.

I claim:

1. A device for occluding a defect in septal tissue, comprising:
   a first side adapted to be disposed on one side of septal tissue with a defect and a second side adapted to be disposed on an opposite side of the septal tissue with a defect,
   an elongate center joint disposed between the first and second sides,
   said first and second sides adapted to occlude the defect upon deployment at the delivery location,
   said first and second sides each comprising a plurality of non-overlapping wires,
   wherein said wires form loops that extend from a center axis, the loops having inner ends proximate to the center axis and outer ends distal from the center axis, and adjacent segments of said loops are connected to each other along a generally radially extending length of the pair of adjacent segments including a point between the inner ends and the outer ends of the respective loops.

2. The device of claim 1, wherein said device is adapted to center around an asymmetrically-located defect.

3. The device of claim 1, wherein said adjacent segments are welded.

4. The device of claim 1, wherein said device includes a material selected from the group consisting of metals, shape memory materials, alloys, polymers, bioabsorbable polymers, and combinations thereof.

5. The device of claim 4, wherein said device includes nitinol.

6. The device of claim 1, wherein at least one of said first and second sides further comprises a tissue scaffold.

7. The device of claim 6, wherein said tissue scaffold includes a material selected from the group consisting of polyester fabrics, Teflon-based materials, polyurethanes, metals polyvinyl alcohol (PVA), extracellular matrix (ECM) or other bioengineered material, synthetic bioabsorbable polymeric scaffolds, collagen, and combinations thereof.

8. The device of claim 7, wherein said tissue scaffold includes nitinol.

9. The device of claim 7, wherein said tissue scaffold is attached to said loops of said at least one side.

10. The device of claim 1, wherein said first and second sides are connected by an intermediate joint.

11. The device of claim 10, wherein said intermediate joint is positioned so as to minimize distortion to the septal tissue surrounding the defect.

12. The device of claim 11, wherein said intermediate joint is positioned at an angle θ from said second side and wherein said angle θ is greater than 0 degrees and less than about 90 degrees.

13. A device for occluding a defect in septal tissue, comprising:
   a first side adapted to be disposed on one side of septal tissue with a defect and a second side adapted to be disposed on an opposite side of the septal tissue with a defect,
   an elongate center joint disposed between the first and second sides,
   said first and second sides adapted to occlude the defect upon deployment at the delivery location,
   said first and second sides each comprising a plurality of non-overlapping wires, wherein said wires form loops that extend from a center axis, the loops having inner ends near to the center axis and outer ends further from the center axis, and adjacent segments of said loops are connected to each other along a generally radially extending length of the pair of adjacent segments including a point between the inner ends and the outer ends of the respective loops.

14. The device of claim 13, wherein said device is adapted to center around an asymmetrically-located defect.

15. The device of claim 13, wherein said adjacent segments are welded.

16. The device of claim 13, wherein said device includes a material selected from the group consisting of metals, shape memory materials, alloys, polymers, bioabsorbable polymers, and combinations thereof.

17. The device of claim 16, wherein said device includes nitinol.

18. The device of claim 13, wherein at least one of said first and second sides further comprises a tissue scaffold.

19. The device of claim 18, wherein said tissue scaffold includes a material selected from the group consisting of polyester fabrics, Teflon-based materials, polyurethanes, metals, polyvinyl alcohol (PVA), extracellular matrix (ECM) or other bioengineered material, synthetic bioabsorbable polymeric scaffolds, collagen, and combinations thereof.

20. The device of claim 19, wherein said tissue scaffold includes nitinol.

21. The device of claim 19, wherein said tissue scaffold is attached to said loops of said at least one side.

22. The device of claim 13, wherein said first and second sides are connected by an intermediate joint.

23. The device of claim 22, wherein said intermediate joint is positioned so as to minimize distortion to the septal tissue surrounding the defect.

24. The device of claim 23, wherein said intermediate joint is positioned at an angle $\theta$ from said second side and wherein said angle $\theta$ is greater than 0 degrees and less than about 90 degrees.

* * * * *